(12) United States Patent
Griffith et al.

(10) Patent No.: US 6,645,715 B1
(45) Date of Patent: Nov. 11, 2003

(54) ARTIFICIAL CORNEA

(75) Inventors: May Griffith, Ottawa (CA); Mitchell Watsky, Arlington, TN (US); Charles J. Doillon, Québec (CA); Ying Song, Philadelphia, PA (US)

(73) Assignees: University of Ottawa, Ottawa (CA); Universite Laval, Quebec City (CA); University of Tennessee Research Corp., Knoxville, TN (US)

( * ) Notice: Subject to any disclaimer, the term of this patent is extended or adjusted under 35 U.S.C. 154(b) by 442 days.

(21) Appl. No.: 09/624,909

(22) Filed: Jul. 24, 2000

Related U.S. Application Data

(63) Continuation of application No. PCT/CA99/00057, filed on Jan. 25, 1999.

(30) Foreign Application Priority Data

Jan. 23, 1998 (CA) ............................................. 2227827

(51) Int. Cl.$^7$ .............................. A01N 1/02; A61F 2/14
(52) U.S. Cl. ........................ 435/1.1; 435/371; 623/5.11; 623/5.16
(58) Field of Search .................. 435/1.1, 371; 623/5.11, 623/5.16

(56) References Cited

U.S. PATENT DOCUMENTS

| | | | |
|---|---|---|---|
| 5,374,515 A | 12/1994 | Parenteau et al. | |
| 5,585,265 A | 12/1996 | Kahn et al. | |

FOREIGN PATENT DOCUMENTS

| | | | |
|---|---|---|---|
| EP | 363125 | 4/1990 | |

OTHER PUBLICATIONS

Anderson, J.A., Richard, N.R., Rock, M.E. and Binder, P.S. (1993). Requirement for vitamin A in long–term culture of human cornea. Invest. Ophthalmol. Vis. Sci. 34: 3442–3449.

Araki–Sasaki, K., Ohashi, Y., Sasabe, T., Hayashi, K., Watanabe, H., Tano, Y. and Handa, H. (1995). Invest. Ophthalmol. Vis. Sci. 36: 614–621.

Assil, K.K. and Quantock, A.J. (1993). Wound healing in response to keratorefractive surgery. Surv. Ophthalmol. 38: 289–302.

Bagley, D.M., Bruner, L.H., deSilva, O., Cottin, M., O'Brien, K.A.F., Uttley, M. and Walker, A.P. (1992). An evaluation of five potential alternatives in vitro to the rabbit eye irritation test in vivo. Toxicol. in Vitro 6: 275–284.

Bockman, C., Griffith, C.M., and Watsky, M.A. (1998). Characterization of whole cell ionic currents from cultured human corneal epithelial cells. Invest. Ophthalmol. Vis. Sci. 39: 1143–1151.

Borenfreund, E. and Puerner, J.A. (1985). Toxicity determined in vitro by morphological alterations and neutral red absorption. Toxicol. Lett. 24: 119–124.

Bodnar, A.G., Ouellete, M., Frolkis, M., Holt, S.E., Chiu, C.P., Morin, G.B., Harley, C.B., Shay, J.W., Lichtsteiner, S., and Wright, W.E. (1998). Extension of life–span by introduction of telomerase into normal human cells. Science 279: 349–352.

Burton, A.B.G., York, M. and Lawrence, R.S. (1981). The in vitro assessment of severe eye irritants. Food Cosmet. Toxicol. 19: 471–480.

Collin, H.B., Anderson, J.A., Richard, N.R. and Binder, P.S. (1995), In vitro model for corneal would healing: organ cultured human corneas. Curr. Eye Res. 14: 331–339.

Doughman, D.J. (1980). Prolonged donor cornea preservation in organ culture: long term clinical evaluation. Trans. Am. Ophthlmol. Soc. LXXCVIII: 624–628.

Draize, J.H., Woodard, G. and Calvery, H.O. (1944). Methods for the study of irritation and toxicity of substances applied topically to the skin and mucuous membranes. J. Pharmacol. Exp. Ther. 82: 377–390.

Galer, D.M. (1992). A collaborative approach to the evaluation of alternatives to the eye irritation test using chemical intermediates. In Vitro Cell Dev. Biol 28: T–2.

Gautheron, P., Dukic, M., Alix, D. and Sina, J.F. (1992). Bovine corneal opacity and permeability test: An in vitro assay of ocular irritancy. Fund. Appl. Toxicol. 18: 442–449.

Gordon, V.C. (1992). Utilization of biomacromolecular in vitro assay systems in the prediction of in vivo toxic responses. Lens and Eye Toxicity Res. 9: 211–227.

Griffith, C.M. and Hay, E.D. (1992). Epithelial–mesenchymal transformation during palatal fusion: carboxyfluorescein traces cells at light and electron microscopic levels. Development 116: 1987–1099.

Griffith, M. (1997). Midkine and secondary neurulation. Teratology 55: 213–223.

(List continued on next page.)

*Primary Examiner*—James Ketter
(74) *Attorney, Agent, or Firm*—Howard Eisenberg, Esq.

(57) ABSTRACT

The invention provides an in vitro avascular human corneal equivalent that comprises immortalized human cell lines. As these corneal equivalents are in vitro models, they are maintained in an incubator throughout the testing period, thereby eliminating the problems and expense associated with animal care. The corneal equivalent is preferably surrounded by a matrix in which angiogenesis (formation of capillary-like structures) can occur in vitro. This surrounding matrix has the potential to play the role of a pseudo-sclera, allowing the in vitro assessment of the cornea's angiogenic reaction to any substance or injury. Furthermore, the model is capable of being produced easily, is physiologically functional and can give predictable and quantifiable results when submitted to various drugs, chemicals and/or physical trauma. Modifications can be made, such as the use of primary donor cells instead of cell lines; and the physical and chemical treatments of the matrix material to make the constructs suitable for use in transplantation.

33 Claims, 29 Drawing Sheets

(4 of 29 Drawing Sheet(s) Filed in Color)

OTHER PUBLICATIONS

Halbert C.L., Demers, G.W. and Galloway, D.A. (1991). The E7 gene of human papillomavirus type 16 is sufficient for immortalization of human epithelial cells. J. Virol. 65: 473–478.

Halbert, C.L., Demers, G.W. and Galloway, D.A. (1992). The E6 and E7 genes of human pappiloma virus type 6 have weak immortalizing activity in human epithelial cells. J. Virol. 66: 2125–2134.

Heitzmann, J. Binder, P.S., Kassar, B.S., and Nordan, L.T. (1993). The correction of high myopia using the excimer laser. Arch. Ophthalmol. 111: 1627–1634.

Kahn, C.R., Young, E., Lee, I.H. and Rhim, J.S. (1993). Invest. Ophthalmol. Vis. Sci. 34: 1983–1990. Human corneal epithelial primary cultures and cell lines with extended life span: in vitro model for ocular studies.

Martin, K.M. and Stott, C.W. (1992). The trans–epithelial permeability assay as an in vitro assay for predicting ocular irritation of surfactant formulations. In Vitro Cell Dev. Biol. 28: T–1032.

Minami, Y., Sugihara, H. and Oono, S. (1993). Reconstruction of cornea in three–dimensional collagen gel matrix culture. Invest. Ophthal. Vis. Sci. 34: 2316–2324.

Osborne, R., Perkins, M.A. and Roberts, D.A. (1995). Development and intralaboratory evaluation of an in vitro human cell–based test to aid ocular irritancy assessments. Fund. Appl. Toxicol. 28: 139–153.

Rae, J.L., Cooper, K.E., Gates, P. and Watsky, M.A. (1991). Low access perforated patch recordings using amphotericin. Brit. J. Neurosci. Methods 37: 15–26.

Richard, N.R., Anderson, J.A., Weiss, J.L. and Binder, P.S. (1991). Air/liquid corneal organ culture: a light microscopic study. Current Eye Res. 10: 739–749.

Schermer, A., Galvin, S. and Sun, T.T. Differentiation–related expression of a major 64K corneal keratin in vivo and in culture suggests limbal location of corneal epithelial stem cells. J. Cell Biol. 103: 49–62.

Sirois E., Cote, M.F. and Doillon, C.J. (1993). Growth factors and biological support for endothelial cell lining: in vitro study. Int. J. Artificial Organs 16: 609–619.

Southern, P.J. and Berg, P. (1982). Transformation of mammalian cells to antibiotic resistance with a bacterial gene under control of the SV40 early region promoter. J. Molec. Appl. Gen. 1: 327–341.

Watsky, M.A., McDermott, M.L. and Edelhauser, H.F. (1989). In vitro corneal endothelial permeability in rabbit and human: The effects of age, cataract surgery and diabetes. Exp. Eye Res. 49: 751–767.

Watsky, M.A., McCartney, M.D., McLaughlin, B.J. and Edelhauser, H.F. (1990). Corneal endothelial junctions and the effect of Ouabain. Inv. Ophthal. Vis. Sci. 31: 933–941.

Watsky, M.A., Cooper, K.E. and Rae, J.L. (1992). A transient outwardly rectifying potassium current in the rabbit corneal endothelium. J. Membrane Biol. 128: 123–132.

Zieske, J.D., Mason, V.S., Wasson, M.E., Meunier, S.F., Nolte, C.J.M., Fukai, N, Olsen, B.R. and Parenteau, N.L. (1994). Basement membrane assembly and differentiation of cultured corneal cells: Importance of culture environment and endothelial cell interaction. Exp. Cell Res. 214: 621–633.

Moczar, Madeleine, et al. Effect of aldehyde in the hydration potential of the corneal stroma. C.R. Acad. Sci., Paris, Ser. D. (1969) 268(22): 2734–6.

CORNEA RECONSTRUCTED WITH TRANSFORMED EPI CELLS

CORNEAL ENDOTHELIAL CELL LINES (IN SITU HYBRIDIZATION)

TYPE VIII COLLAGEN - AS PROBE

SENSE CONTROL

ARROWHEADS = BLOOD VESSELS

FIG. 20A
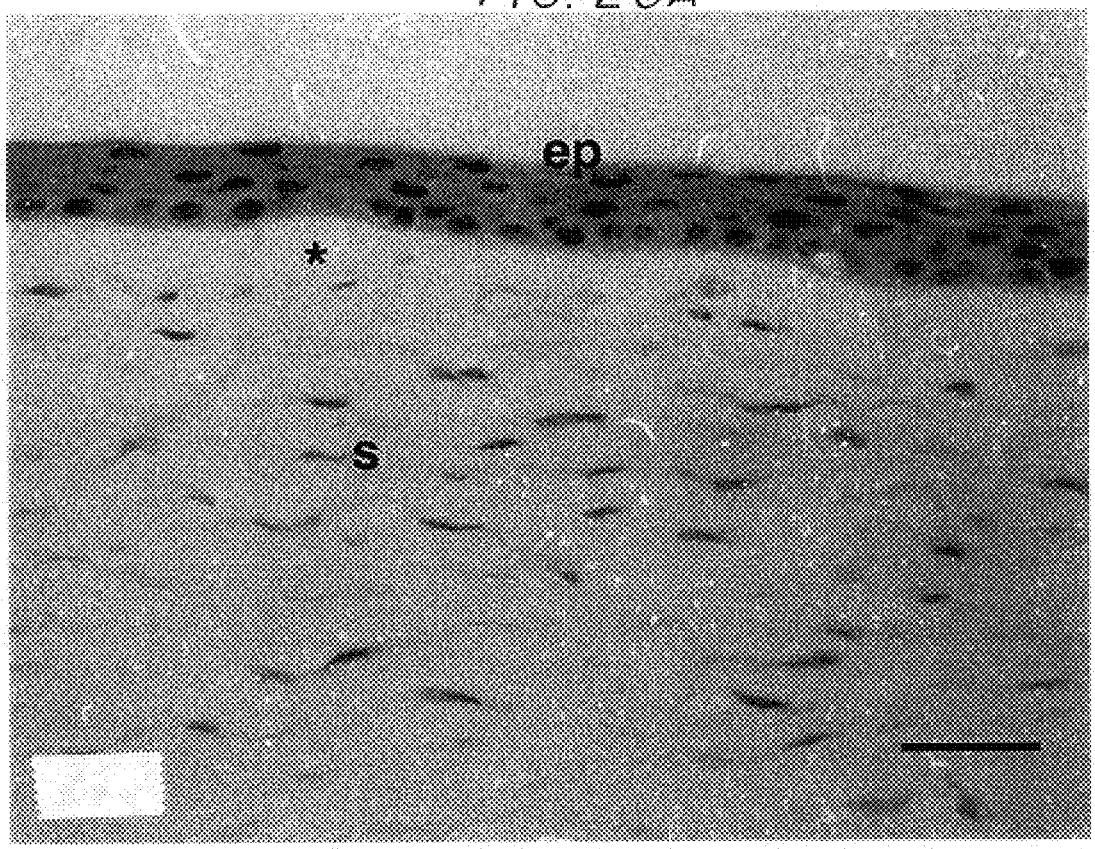
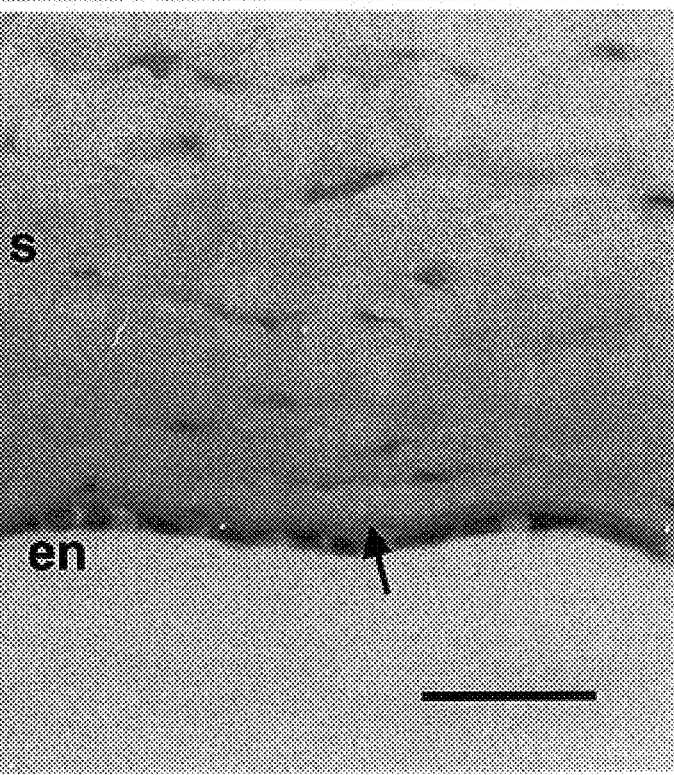
FIG. 20B

ARTIFICIAL CORNEA

This application is a continuation of PCT Application No. PCT/CA99/00057 filed on Jan. 25, 1999.

FIELD OF THE INVENTION

The invention is in the field of tissue engineering and culture systems and is directed primarily towards reconstruction of in vitro cell-based models for use as animal alternatives in irritancy, toxicity and drug efficacy testing. In particular, the invention relates to an artificial cornea.

BACKGROUND OF THE INVENTION

Animal tests are used for screening new chemicals, drugs, finished products or their ingredients for potential ocular irritancy. The historic test that is still in widespread use is the Draize rabbit eye irritancy test. The Draize test was developed in 1944 and involves the introduction of 0.1 ml of a test substance into the lower conjunctival sac of albino rabbit eyes (Draize et al. 1944). Responses of the cornea, conjunctiva and iris are graded using a numerical scoring system. The cornea is scored for opacity that is induced by irritants. The conjuctivum is scored for an angiogenic response (such as redness caused by blood vessel dilation) while the iris gives a neurological response (i.e., contraction or dilation). Of these, an indication of corneal clarity/opacity is the most relied upon indicator for irritancy. Although still regarded as the definitive test available, the Draize test suffers not only from strong resistance from the public, but also because the rabbit eye responds differently to various traumas than does the human eye.

Animal testing is also used in the development of ophthalmic drugs. Again, differential responses between animal models, such as rabbits and humans, are well documented for drugs ranging from analgesics for pain and antibiotics, to steroid and non-steroid preparations that modify wound healing responses.

Enucleated whole eyeballs from rabbits and cattle have been tested as possible Draize alternatives. Among them are the Bovine Eye Assay which measures corneal opacity/permeability from Merck Sharp and Dome laboratories. While enucleated rabbit and bovine eyes have shown a capacity to handle and identify severely irritating substances over a wide range of physical forms and solubilities, they are less sensitive for resolving responses to very mild and moderately irritating substances (Burton et al. 1981; Gautheron et al. 1992). In addition, these are animal derived tissues and therefore have the same accuracy problems and difficulty with extrapolation to humans as the Draize test. Moreover, the very short term viability of these corneas (tests are done on the day of enucleation) will not allow for longer term screening of more chronic effects of the milder test substances.

Organ cultured human corneas can be used for testing. Richard et al. (1991), Anderson et al. (1993) and Collin et al. (1995) have successfully organ cultured freshly obtained whole human corneas, allowing for investigations to be carried out on whole corneas. However, organ cultured corneas have a finite lifespan. The longest time recorded is 21 days (Anderson et al. 1993). More importantly, the availability of donors is sporadic and donor corneas are too heterogeneous to be useful as a practical model for drug testing.

Other alternatives that have been developed include the EYTEX™ test from In Vitro International (formerly Ropak Laboratories) which is based on the quantification of opacity produced in a synthetic protein matrix on exposure to chemical irritants (Gordon, 1992); the Keratinocyte Neutral Red Uptake Bioassay from Clonetics Corporation based on the methodology of Borenfreund and Puerner (1985), the MTT assay using living skin equivalent from Advanced Tissue Sciences (Osborne et al. 1995), and the Chorioallantoic membrane vascular assay (Bagley et al., 1992). Transepithelial permeability assay can also be used as an in vitro assay for predicting ocular irritancy using MDCK cells (Martin and Stott, 1992). Others use an agar diffusion cytolysis as an alternative screen for the prediction of a corrosive ocular response using rabbit cornea fibroblasts (Galer, 1992).

Results indicate that while it may not be possible to use a single test to classify compounds as to irritation potential, some of the alternative test models may be useful in prioritizing and reducing the number of in vivo irritation tests conducted. However, all of the tests are dependent upon continued rabbit eye testing as definitive tests and also to develop validation databases to aid interpretation of the in vitro data.

Researchers have been attempting to reconstruct corneas in vitro from cell lines. Individual human corneal epithelial layers have been successfully maintained in culture as a stratified epithelium by Kahn et al. (1993) and Araki-Sasaki et al. (1995). These investigators had used corneal epithelial cell lines that were immortalized using a hybrid SV40-adenovirus. Successful reconstructions of corneas comprising the three main layers have also been recently reported by Minami et al. (1993) and Zieske et al. (1994). These corneas were reconstructed from either passaged primary cells from bovine (Minami et al. 1993), or mixed cultures of primary rabbit epithelial and stromal cells and an immortalized mouse endothelial cell line (Zieske et al. 1994).

To date, there have been no reports of successfully reconstructed human corneas based fully on human cell lines while mimicking the physiology of the human cornea and surrounding tissue.

Media used in preparing artificial corneas, or in culturing whole corneas, must be carefully selected to avoid detrimental effects to the desired process. Certain serum proteins will affect wound healing and hence a serum-free medium is desirable to allow optimal control of experimental conditions. Disclosed herein is a serum-free medium that may be used to prepare the cornea of the present invention, as well as for culturing whole corneas.

SUMMARY OF THE INVENTION

The present invention provides an artificial mammalian cornea which comprises:
  a) an endothelium comprising primary or immortalized mammalian endothelium cells;
  b) a stromal matrix;
  c) an epithelium comprising primary or immortalized mammalian epithelium cells; and
  d) at least one layer selected from Bowman's membrane and Descemet's membrane.

The present invention also provides a method for preparing an artificial mammalian cornea which comprises:
  a) growing an endothelium which comprises primary or immortalized mammalian endothelium cells;
  b) optionally layering a Descemet's membrane on the endothelium;
  c) forming a stromal matrix on the endothelium or on the Descemet's membrane, if present;

d) optionally layering a Bowman's membrane on the stromal matrix; and e) growing an epithelium, which comprises primary or immortalized mammalian epithelium cells, on the stromal matrix or on the Bowman's membrane, if present;

wherein at least one of Bowman's membrane and Descemet's membrane is present.

The present invention further provides a method for preparing an artificial mammalian cornea which comprises:

a) growing an epithelium which comprises primary or immortalized mammalian epithelium cells;

b) optionally layering a Bowman's membrane on the epithelium;

c) forming a stromal matrix on the epithelium or on the Bowman's membrane, if present;

d) optionally layering a Descemet's membrane on the stromal matrix; and e) growing an endothelium, which comprises primary or immortalized mammalian endothelium cells, on the stromal matrix or on the Descemet's membrane, if present;

wherein at least one of Bowman's membrane and Descemet's membrane is present.

The present invention also provides a commercial package which comprises:

a) the cornea as described herein, and b) instructions for its use for testing a substance for ocular irritancy, toxicity or drug efficacy, or transplantation.

The present invention also provides a serum-free culture medium which comprises at least one of each of a protease inhibitor, a growth factor, a substance which mediates the growth factor and a free-radical scavenger, and preferably a substance which prevents cellular contraction, as well as instructions for use of the medium in culturing a cornea, preferably a human cornea, in vitro.

The present invention also provides an artificial sclera which comprises primary or immortalized mammalian angiogenic cells.

Gene transfer and tissue culture techniques have been used to construct a cornea from immortalized human cell lines that is analogous to the human cornea in vivo. The corneal equivalent is preferentially surrounded by a sclera capable of mimicking inflammation responses.

Various different gene constructs have been introduced into the immortalized cell lines by transfection and/or retroviral infection to either overexpress, or block expression (antisense constructs) of, gene products in order to mimic different pathological conditions that occur in the cornea. This allows the development of in vitro corneal disease models for studying drug treatment efficacy.

The model can also be modified to render it suitable for use in transplantation. Also described is a medium that can be used to start and maintain cultures of primary cells and cell lines from cornea and other tissues. The medium is also suitable for the culture of corneas, both artificial and natural, in the absence of serum.

The artificial cornea is preferably surrounded by a matrix in which angiogenesis (formation of capillary-like structures) can occur in vitro. The artificial cornea is physiologically and functionally similar to the human cornea and has the potential to respond to ocular irritants, drugs and injuries. The surrounding angiogenic material plays the role of pseudo-sclera and thereby provides the ability to assess in vitro the angiogenic reaction to any chemical irritants, drugs or any injuries. The invention extends to a method for making the artificial cornea and a method for using the artificial cornea. Preferably, the corneal or scleral cells used, whether primary or immortalized, are of human origin.

The invention also provides a serum-free medium that has been used to successfully start and maintain the cell lines, as well as the artificial corneas. The medium may also be used in reconstruction of other body tissues that could be used as complementary in vitro models for alternative models to animal testing.

The artificial cornea can also be modified for transplantation by modification of the matrix compounds by physical and chemical treatments, and incorporation of matrix proteins or essential amino acid sequences and/or growth factors. Primary cells can be used until the safety of cells containing viral constructs for transplantation has been determined. In addition, cells from one or more layers may be omitted to allow for the host/patient's cells to repopulate the transplanted matrix material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention and its preferred embodiments may be better-understood with reference to the following drawings.

FIG. 20 shows human corneas cultured for 3 weeks. A. Epithelium, showing uniformed stratified squamous epithelia (ep) of five layers. The underlying Bowman's membrane (*) is present. The stroma (s) shows no signs of edema. Bar, 60 $\mu$m. B. Endothelial layer (en) and Descemet's membrane (arrow) were also intact.

DETAILED DESCRIPTION OF THE INVENTION

Figures 1A, 1B:
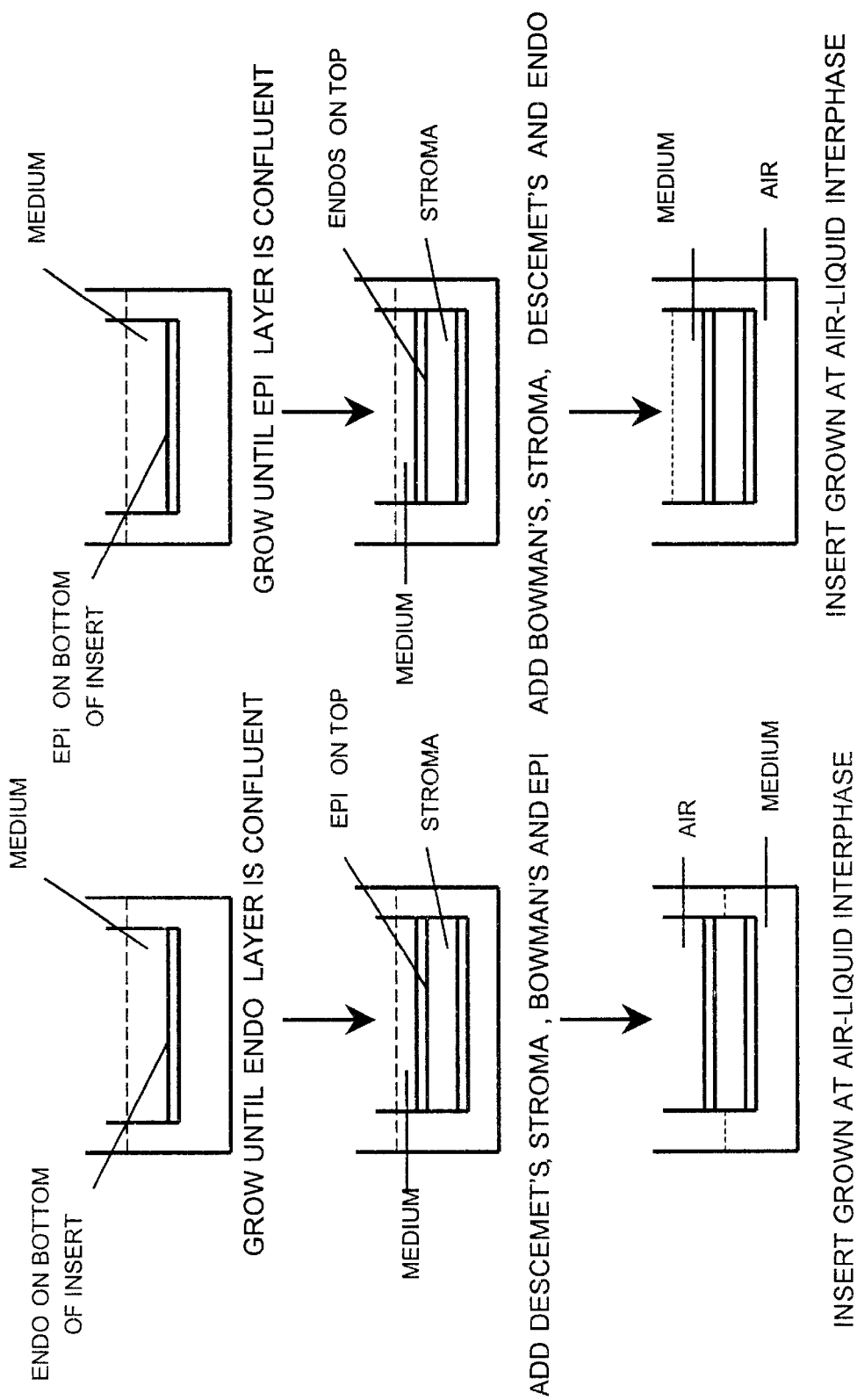
FIGS. 1a and 1b show methods of reconstruction of a cornea in vitro.

The invention comprises mammalian, preferably human, corneal cell lines, either primary or immortalized, that have been reconstructed to mimic the human cornea in structure, physiological functioning and responses to drugs, chemicals and other compounds. The reconstructed cornea can be constructed on its own or with a surrounding sclera. The latter is preferred when testing of angiogenic responses are required (e.g. in mimicking conditions when vascular invasion of the cornea occurs due to irritation or injury from physical or chemical sources or disease). The reconstructed cornea with/without sclera can be cultivated either in serum-supplemented medium or a serum-free medium such as the one described herein.

Corneal Cell Lines

Cell lines are produced from each of the main corneal layers: epithelium, stroma and endothelium. The epithelial and endothelial layers are isolated by scraping post-mortem human corneas with a surgical Gill knife. Pieces from each of these layers are placed separately in culture medium containing a 1:1 mixture of Medium 199 (GIBCO, Burlington, Canada): Optisol (Chiron Ophthalmics, Irvine, Calif.) supplemented with 10% foetal bovine serum (FBS; GIBCO), 1% insulin-transferrin-selenium (ITS; Becton Dickinson Canada, Mississauga, Canada) and 0.1% gentamicin (GIBCO). The serum-free medium disclosed herein can also be used, as well as any conventional serum-based or serum-free growth medium.

The pieces are dissociated by pipetting up and down and the cells are left to grow out onto the tissue culture dish. The stroma, which is scraped clean of residual epithelium and endothelium is cut into pieces and digested with 0.25% collagenase at 37° C. for several hours to loosen the matrix and release stromal keratocytes. The stromal pieces are further broken down by either pipetting or passing through a syringe. The collagenase is removed by aspiration after centrifugation of the mixture. The dissociated stroma is then plated onto tissue culture dishes and supplemented with the serum-free medium described herein.

The cells take from two days to over a week to settle and multiply. After colonies are present, the medium is aspirated and replaced with Medium 199, 10% FBS and 1% ITS. Colonies of outgrowing cells with the appropriate morphology for the cell type are picked out and expanded. These are then used for producing immortalized cell lines.

Cell lines for reconstruction can be immortalized in a variety of ways. Current methods include, but are not limited to, transfection with viral oncoproteins (Kahn et al., 1993), infection with retrovirus containing HPV E6 and E7 genes (Halbert et al., 1991, 1992) and methods that would reactivate cellular telomerase activity (Bodnar et al., 1998). Cell lines could also include those that contain genes conferring immortality (or transformation) which can be turned "on" and "off" in regulated gene expression systems (eg. Clonetech's Tet-On/Tet-Off™).

Cells used in the present invention were preferably immortalized in two ways. Some primary cells (endothelial, stromal, epithelial) were transfected with a combination of plasmids that contained the SV40 large T antigen, pSV3neo (Southern and Berg, 1982) and the AD5-E1A region (gift from Dr. Steve Whelan), using standard calcium phosphate transfection, using a BES buffer. After transfection, the cells were returned to their regular medium (M199, 10% FBS, 1% ITS) and then passaged just before confluence. Resistance to G418 was used to select for successful transfectants. For corneal cells, 1 mg/ml G418 was added to the culture medium until the control cells died.

Corneal epithelial cell lines were exposed to sodium dodecyl sulfate (SDS) to characterise the changes in mRNA expression of early response genes such as c-fos and c-jun, cytokines probably involved with corneal wound healing such as interleukins (IL-1a and IL-6), basic fibroblast growth factor (bFGF), vascular endothelial growth factor (VEGF) and epidermal growth factor (EGF), and matrix molecules that are elaborated during healing such as collagens types I, III and V.

Reverse transcription-polymerase chain reaction (RT-PCR) was used to examine changes in expression of the above genes in corneal epithelial cell lines compared to primary cells, and in artificial corneas compared to human corneas from the eye bank after exposure to a detergent SDS. The cells were exposed to 0.02% SDS in M199 for 2 minutes. Corneas were treated with 5% SDS in M199. Controls were dosed with M199 only. RT-PCR was performed on RNA from cells and corneas obtained at different time points after injury. Semi-quantitative analyses were conducted by introducing the housekeeping gene, glyceraldehyde-3-phosphate dehydrogenase (GAPDH) as an internal control and by Southern analysis. PCR products were sequenced to confirm their identity.

Results are shown in FIG. 26. Baseline levels of the 10 mRNAs examined were established in control epithelial cells and corneas (n> or =6 for each time point). Expression of c-fos and c-jun was significantly increased within 1 hour of SDS injury in both primary epithelial cells and epithelial cell lines. Expression of c-fos returned to baseline levels by the end of 24 hours, but c-jun expression remained high until day 6 after injury. There was also increased expression in IL-1a, IL-6, collagen I and collagen V mRNA. However, changes in MRNA expression for bFGF, VEGF, EGF and collagen III were non-significant.

The pattern of changes in gene expression in SDS-treated reconstructed corneas (n=6) was similar to that in monolayers of epithelial cells. However, these changes were more marked in the reconstructed whole corneas than in the epithelial monolayers.

Both cells in monolayer cultures and whole corneas showed changes in gene expression following exposure to SDS. These changes in established cell lines were comparable to those in primary cells. Reconstructed corneas, like human eye bank corneas, also responded to SDS exposure with changes in gene expression.

Other cells (epithelial, stromal, endothelial) were infected with an amphotropic recombinant retrovirus that contains HPV16 genes E6 and E7 (Halbert et al., 1991, 1992). The producer cell line PA317LXSN 16E6E7 was obtained from the ATCC. Essentially the corneal cells were infected with serially diluted viral-containing conditioned culture supernatants from the producer cells in the presence of 10 µg/ml polybrene (Sigma, St. Louis, Mo., USA). After 24 hours of exposure to the virus, the viral supernatant was removed and the cells cultured, passaged once and then immortalized cells were selected for by G418 resistance.

Other genes have been incorporated into the cell lines. For example, the gene for green fluorescent protein (GFP), a fluorescent reporter molecule, available in expression vectors (eg. from Clonetech) was incorporated into the cell lines by transfection followed by selection. GFP-producing cell lines can be tracked within the reconstructed cornea in wound healing or other lineage studies.

Electrophysiological Screening of Cells

All three types of cell lines were initially screened for functional morphological criteria. Cells of appropriate morphology were screened for functional electrophysiologic similarities to human cornea cells by use of patch clamp technology to examine ionic currents. The patch clamp technique is disclosed in numerous scientific articles, including Rae (1991) and Watsky (1992), which are incorporated herein by reference. Cells that were similar to corneal cells morphologically and electrophysiologically were screened for expression of the appropriate biochemical markers. Cells that were deemed similar to those of the cornea were then given a final test by performing an initial reconstruction of the cornea only.

EXAMPLE 1

Cells having the appropriate morphology were screened to compare the electrophysiologic characteristics of the cells to non-transfected cells. In this way, it was verified that the cells were truly immortalized and that the cells were not transformed, that is that they retained the phenotypic characteristics of normal cultured cells. Cells that passed these tests were deemed suitable for inclusion in the artificial cornea of the invention, as long as they passed subsequent immunohistochemical and DNA screens. Cells that did not have the appropriate electrophysiological characteristics were not included in the invention.

Single cells for patch clamp analysis of transfected and non-transfected cells were obtained by washing cultured cells free of culture medium using PBS containing 0.53 mM EDTA and then incubating with $Ca^{+2}$ and $Mg^{+2}$ free Hanks' balanced salt solution (GIBCO) containing 0.05% trypsin and 0.53 mM EDTA for 2 minutes at 37° C. in a 5% $CO_2$ incubator. Loose cells were aspirated into a Pasteur pipette and transferred into a conical tube containing Media 199 (Sigma, St. Louis, Mo.) supplemented with 10% FCS (Sigma, St. Louis, Mo.). Isolated cells were transferred to an inverted microscope mounted with an external stage, placed into an acrylic chamber filled with Ringer's solution, and allowed to settle and attach to the glass bottom.

Macroscopic currents in single cells were examined using the perforated-patch configuration of the whole-cell patch-clamp technique with amphotericin B as the perforating agent. The composition of the patch pipette in millimolar was 145 potassium methanesulfonate, 2.5 NaCl, 2.5 $CaCl_2$, 5 HEPES, and 250 mg/ml amphotericin B. Patch pipettes were fabricated from KG-12 capillary glass, coated with Sylgard (Dow Corning, Midland, Mich.) and fire polished. Currents were recorded at room temperature using a patch-clamp amplifier operated by Gateway 486DX2 computer (Gateway 2000, Sioux City, S. Dak.) loaded with pCLAMP software (Axon 200A, Axon Instruments, Foster City, Calif.) for the generation of voltage-clamp protocols. Current recordings were capacity compensated using the amplifier circuitry, sampled between 2 to 5 kHz, filtered between 1 to 2 kHz, and subsequently analyzed with the software program. Voltage-clamp protocols were repeated at least three times to obtain the average current response to a voltage pulse. Current voltage (I–V) relationships were corrected for the junction potential generated by the pipette solution and the amphotericin B-induced Donnan potential by subtracting the difference between the reversal potential of tail currents measured in symmetrical $K^+$ solutions and the 0 mV potential.

The following patch-clamp electrophysiologic tests were performed on and compared in both cultured non-transfected cells and cultured transfected (immortalized) cells. In the description that follows, tests performed on human corneal epithelial cells are described as an example of the comparative testing. It is to be understood, however, that the electrophysiological testing may be performed on any cell which is considered for inclusion in the artificial cornea of the invention, which cell is preferably compared electrophysiologically to cells which are normally found in the analogous layer of the natural cornea.

EXAMPLE 1.1

Whole Cell Current Appearance of Nonselective Cation Current

Single cells were bathed in NaCl or KCl based Ringer's solution. Individual cells were held at a resting voltage of 0 mV and then had their membrane potential relative to ground clamped to different voltages from –80 mV to 130 mV in 15 mV steps, with each step followed by a return to the 0 mV resting voltage. The current produced by the cell at each voltage was measured and plotted over time to produce a graph representative of the steady-state whole-cell nonselective current appearance of the cell. In both NaCl and KCl Ringer's solution, human corneal epithelial cells typically had a similar outwardly rectifying current which was relatively noisy and showed no inactivation. No tail current was observed in either solution with this protocol. The current was not sensitive to the transmembrane holding voltage, 1 mM external barium or 1 mM external gadolinium.

EXAMPLE 1.2

Current Voltage Relationships

The current to voltage (I–V) relationship of the steady state current responses produced above was plotted and showed that, for human corneal epithelial cells, the depolarization voltage required for current activation was approximately 50 mV and that the I–V relationship for activation of the current was similar whether the cells were bathed in NaCl or Kcl.

EXAMPLE 1.3

Ion Selectivity of the Current

The outward current of the tested cells was activated with a depolarizing voltage pulse (100 mV) followed by a series of voltage steps to generate a family of instantaneous tail current responses. The instantaneous tail I–V relationship was plotted with the current (I) on the y-axis and voltage (V) on the x-axis. From this plot, the membrane potential ($E_{rev}$) where the outward current reversed to an inward current was determined. The $E_{rev}$ of a cell is characteristic of the ions that carry a select current in the cell. The noisy outward current of cultured human corneal epithelial cells reversed at approximately –5 mV, indicating the equal involvement of $Na^+$ and $K^+$ ions in carrying current through nonselective cation channels.

EXAMPLE 1.4

Pharmacological Activators

The tests of examples 1.1, 1.2, and 1.3 were repeated following the addition of 100 $\mu$M flufenamic acid (FFA) to the NaCl Ringer's bath. In cultured human corneal epithelial cells, addition of FFA elicited a current causing a more than 10-fold increase in the maximum outward current present in the cells not exposed to FFA. The I–V plot showed that the FFA-stimulated current activated at about –60 mV. The FFA response was reversible and repeatable in the same cell. The addition of 3 mM tetraethylammonium (TEA) blocked the FFA-activated current and produced an I–V relationship substantially the same as for cells in baths lacking FFA. Likewise, the addition of 5 mM $Ba^{+2}$ blocked the FFA-stimulated current.

To determine the ion selectivity of this TEA-sensitive FFA-activated current, cultured human corneal epithelial cells were bathed in NaCl Ringer's solution with 100 $\mu$M FFA and a family of instantaneous tail currents was generated. The same cells were then bathed in NaCl Ringer's solution with 100 $\mu$M FFA and 3 mM TEA and a second family of instantaneous tail currents was generated. An instantaneous tail I–V plot was obtained by digitally subtracting the instantaneous tail responses determined for the same cell bathed with FFA with and without TEA. The $E_{rev}$ for the TEA-sensitive FFA-activated current was calculated to be about −80 mV, close to the −86 mV $E_{rev}$ found for a purely selective K$^+$ selective channel. These results, together with the fact that the FFA-activated current was inhibited by K$^+$ channel blockers TEA and Ba$^{+2}$, demonstrate that the FFA-activated current is carried by K$^+$.

In addition to the above channels, by using patch clamp testing, it has been determined that cultured human corneal epithelial cells may have one or more of the following channels: 1) a second K$^+$ current that is stimulated by FFA and is active only at voltages greater than +10 mV, 2) a rapidly activating inward voltage dependent Na$^+$ current that is observed when the transmembrane potential is held at −90 mV and reaches a peak by 1.5 msec and is almost completely inactivated by 16 msec. This current is not observed when the transmembrane potential is held at 0 mV. 3) An inwardly rectifying K$^+$ current active at voltages between −40 and −80 mV. 4) A second nonselective cation current with characteristics different than the one described in Examples 1.1 to 1.3.

For purposes of making the artificial cornea of the invention, cells are selected which have electrophysiological characteristics of normal, non-transfected, corneal cells and which do not have electrophysiological characteristics which are not present in normal corneal cells. That is, cells were deemed to be suitable for inclusion in the artificial cornea if they possessed at least one of the channels found in normal, cultured corneal cells. For corneal epithelial cells, it is preferable although not essential that they contain the TEA-sensitive FFA-activated current. Preferably, the selected cell contains more than one of the channels, and most preferably, it contains all the channels found in normal cells.

On the other hand, the presence in transfected cells of a channel not found in the normal, non-transfected cell indicates that the cell has been transformed and that its phenotype is no longer the same as that of a normal cell. Therefore, the active presence of these unnatural channels renders a cell unsuitable for inclusion in the artificial cornea of the invention.

The above description of the patch-clamp technique for determining physiologic similarity to corneal cells is provided as an example. One skilled in the art will understand that the method of assessing physiologic similarity to normal cells is immaterial so long as the method permits the determination of similarity to normal cells and the absence or presence of characteristics which indicate transformation.

Morphological and Biochemical Markers

Epithelial and endothelial cells were initially selected for by their cobblestone morphology at confluence. Stromal keratocytes are characteristically fibroblastic and form whorls at confluence. After this initial screening, cells were subjected to immunohistochemical staining for expressed adenovirus E1A or large T antigen. Cells that expressed these proteins were then screened electrophysiologically for similarities to cells that were freshly dissociated from post-mortem corneas and from low passage primary cultures, as described herein. Following the electrophysiological screening, the cells were then screened for expression of the following cell type specific markers. Epithelial cells were stained with the AE5 antibody (ICN) that recognises corneal specific keratin 3, a 64 kD protein found in differentiated corneal epithelial cells (Schermer et al. 1986) as previously described (Bockman et al., 1998). Keratocytes were stained for vimentin, an intermediate filament which is used as a marker for fibroblastic cells, using an antibody from Sigma. Endothelial cells were probed by in situ hybridisation, using run-off RNA transcripts that were labelled with digoxigenin (Griffith, 1997), for expression of alpha2(VIII) collagen, which is produced by the corneal endothelium and is a component of Descemet's membrane.

Reconstruction of the Cornea

The method used is a modification of the protocol described in Zieske et al. (1994). In the present reconstruction method, the insert used is preferably an open-topped plastic cylinder with a semi-porous membrane base. More preferably, either a Costar transwell insert that is pre-coated with type I and type III collagen, or a Milllicell-CM (Millipore) culture insert is used. The latter inserts were coated, preferentially by airbrushing, with type I collagen (Collaborative) in 60% ethanol. For the latter, the coated inserts are air dried and washed with medium several times to neutralize the acidity of the collagen preparation.

Corneal endothelial cells in culture were trypsinized, re-suspended in complete Medium 199 (M199+10% FBS+ 1% ITS+gentamicin) and plated onto the collagen coated insert at a density of 3.0×105 cells per ml. The cells were allowed to grow until about 80% confluence.

Descemet's membrane, which in this case was a mixture of type I and IV collagen and fibronectin in collagen medium (comprising M199, HEPES buffer (200 mM HEPES, 100 mM NaOH), FBS and gentamicin) was then layered on top of the layer of endothelial cells. After this mixture had gelled, the stroma, which is a mixture of type I collagen and 1.5% chondroitin or chondroitin sulphate (other proteoglycans can be substituted to give different consistencies and transparency) in the collagen medium containing 7.5×10$^4$ keratocytes per ml, was layered on top. 1.3 ml of stroma was placed into each insert. It is preferred that the stromal matrix is crosslinked. A preferred crosslinker is gluteraldehyde. The stroma was then allowed to set in the 37° C. incubator for 20 minutes.

Bowman's membrane was then added. This consisted of 150 μl of neutralized type I collagen with 0.1 mg/ml fibronectin and 0.1 mg/ml laminin per insert that was added on top of the stroma and allowed to set.

Finally, 3.0×105 cells per ml epithelial cells were plated on top of the collagen matrix. The culture inserts containing the reconstituted corneas were then cultured until the epithelial cells reached confluence. This usually took one week. Once the reconstruction was completed, the corneas were cultured in serum-free medium. The serum-free medium comprises at least one of each of a protease inhibitor, such as aprotinin; a growth factor, such as EGF or bFGF; a substance which mediates the growth factor, such as a proteoglycan, preferably chondroitin sulphate; a protein such as heparin; and a free radical scavenger, such as superoxide dismutase. Preferably, the serum-free medium further comprises a cell growth promotor that also prevents cellular contraction, such as retinol acetate. A preferred serum-free medium, as shown in Table 1, was used.

TABLE 1

Composition of 2X stock for serum-free medium.

|  | For 100 ml | Final Conc. |
| --- | --- | --- |
| DMEM | 94 ml |  |
| Insulin-transferrin-selenium | 2 ml | 1% |
| Dextran | 2 g | 3 mg/ml |
| Albumax | 0.6 g | 3 mg/ml |
| Chondroitin Sulphate C | 2.7 g | (1.35%) |
| Sodium heparin | 0.018 g |  |

TABLE 1-continued

Composition of 2X stock for serum-free medium.

| | For 100 ml | Final Conc. |
|---|---|---|
| Glutamax-1 (or glutamine) | 2 ml | |
| Gentamicin or antibiotic-antimycotic | 200 µl | |
| JUST BEFORE USE, ADD: | | |
| Aprotinin | 0.14 TIU | 0.07 TIU |
| Hydrocortisone (4 mM - 1.45 mg/ml, MW = 362.5) | 10 µl | 200 nM |
| Putrescine (100 mM - 16.11 mg/ml, MW = 161.1) | 200 µl | 100 µm |
| Progesterone (200 µM - 0.0629 mg/ml, MW = 314.5) | 20 µl | 20 nM |
| Retinol Acetate, H$_2$O soluble (5 mM - 20.4 mg/ml) | 400 µl | 10 nM |
| EGF (10 µg/ml) | 20 µl | 1 ng/ml |
| bFGF | | 50 ng/ml |
| SOD (5 mg/ml - 9 mg in 1.8 ml) | 50 µl | |

1. Make up 1X DMEM medium.
2. Add dextran, Albumax, ITS, sodium heparin, Glutamax and chondroitin C. If necessary, warm gently to dissolve reagents. Filter sterilize.
3. Just before use, add remaining constituents using filter sterilized 1000X stock solutions. (Keep retinol acetate protected from light.)
4. Dilute with 1:1 with 1X DMEM (without anything added). NB. Modifications of the medium by addition/removal of components allows adaptation for culture of other human and animal cells and cell lines.

After the epithelial cells attained confluence, the medium on top of the cornea was removed to create an air-liquid interface. Cell lines that were able to form a 5-layered cornea resembling the human cornea were expanded for use in the corneal-sclera reconstructions.

An alternative method used is to coat the insert with a collagen or fibrin matrix and then seed the epithelial cells, followed by the stroma after epithelial confluence and then the endothelium. Bowman's membrane and/or Descemet's membrane are applied after constructing the epithelial layer and stromal layer, respectively. Air-liquid interface is achieved by withdrawing medium from around the insert and allowing the epithelium to stratify, while maintaining the media supply to the construct from within the insert. This method is preferred when culture time is a factor, because epithelial confluence can be achieved in 1 to 3 days, depending on seeding density, instead of 1 week. Stromal and endothelial cell growth occur concurrently with epithelial stratification.

Serum-free Medium

The above serum-free medium is also able to sustain whole post-mortem corneas in organ culture for at least three weeks and maintain cells in monolayer cultures.

Whole human corneas are traditionally cultured using a submerged culture method that causes swelling, loss of epithelial stratification and other undesirable artifacts. In 1991, Richard and co-investigators reported the successful mostly artifact-free culture of human corneas at an air-liquid interface. While this method worked well with corneas with large attached scleral rims, it was not giving consistently good results with eye bank corneas and corneas harvested for research that had very little scleral rim. In addition, the quality of the results varied with the skill level of the individual performing the culture. A method was therefore devised for organ culturing whole human corneas based on the Richard air-liquid interface culture conditions that would produce consistently good results thereby eliminating the culture method as a variable in studies of corneal wound healing.

Photorefractive keratectomy (PRK) is a technique whereby the excimer laser is used to correct refractive errors in eyesight such as myopia, astigmatism and hyperopia by reshaping the front of the cornea. For myopia treatment, the higher the refractive error to be corrected, the deeper the ablation into the cornea. Problems generally arise when the laser ablation extends into the stroma, and in particular, beyond the anterior one-third of the stroma. Scarring, perceived as hazing which obscures vision, is the major complication following PRK with deep ablations into the stroma (Assil and Quantock, 1993). Results to date indicate that deeper stromal ablations of 150–190 µm for corrections of −11 to −20 dopters (D) have resulted in scarring, and in some practices, up to an incidence of 47% (Heitzmann et al. 1993) The high myopes who have very poor vision, however, are the group of patients for whom excimer laser surgery would be of most benefit, as it would potentially greatly improve their quality of life.

Present wound healing studies have therefore been targeted towards understanding and preventing scarring problems during corneal stromal wound healing.

Due to the morphological and physiological differences in the corneas of animals such as rabbits and humans, human corneas were preferably used in the present studies. Because of this, an in vitro organ model was developed for maintaining the experimental corneas that would simulate the in vivo conditions as much as possible.

Human corneas have traditionally been cultured as submerged cultures, according to the procedure developed by Doughman, 1980. In this procedure, the corneas are inverted, with the epithelium at the bottom and the endothelium close to the level of the medium-air interface. However, while cultures remain viable for up to three weeks, stromal edema is often seen. In addition, epithelial thinning has been observed.

In 1991, Richard et al. reported the successful organ culture of whole human corneas using a method whereby the corneas were maintained at an air-liquid interface for 21 days. Culturing at an air-liquid interface eliminated the problems seen with the submerged cultures. In 1993, the group published the organ culture of human corneas in a serum-free medium containing Vitamin A (retinol), allowing for investigations to be carried out on whole corneas (Andersen et al. 1993).

The method described by Richard et al. (1991) and subsequently used in the group's other studies (Andersen et al., 1993, 1996; Colin et al. 1995) has corneas sitting on top of a Telfon ring that is attached to one side of a culture dish with wax. The corneas were stabilized on the Teflon rings by the curvature of the anterior surface of the eye and the 3–4 mm sclera rings left around the cornea. This method worked for corneas that were removed from whole globes but eye bank corneas and those harvested for research often did not have such a wide scleral rim and did not remain on the rings. In addition, results obtained depended upon the skills of the person performing the culture as the entire endothelial surface may not be in contact with medium due to air bubbles that were trapped under the curvature of the cornea during change from the up to down cycles of the rocker used in the protocol.

Therefore, the present method allows whole corneas to be cultured easily with consistently good results. Both a medium with serum and, preferably, a serum-free medium were used to culture whole human corneas for up to four weeks. In the present study, we examined the wound healing of human corneas in vitro, using our culture system. The corneas were subjected to excimer laser treatment that is identical to what was used and is still used in some centres for the correction of high myopia.

Cultureware

Materials needed include 100×25 mm petri or tissue culture dishes or preferable, square and rectangular dishes such as those manufactured by Nunc (Nalg Nunc International, Naperville, Ill.). The deeper the dish, the better. We have also used autoclavable plastic rings on "legs" to allow media exchange, to hold the cornea in place (FIG. 19A), but this is not necessary for corneas that can be harvested with a scleral rim of at least 3–4 mm.

Organ Culture Medium

Both Medium 199 (Life Technologies, Burlington, Ontario, Canada) with 10% fetal bovine serum (FBS), 1% insulin-transferrin-selenium (ITS, Becton-Dickinson) and antibiotics such as 0.1% gentamicin, and a serum-free medium (Table 1) were used. One percent (1%) agar in complete medium, either with or without serum was used to mimic the aqueous humor of the eye in providing nutrients to the cornea as well as to hold the corneas in place throughout the culture period.

Corneas

Twelve pairs of human corneas with no corneal pathology removed from globes that were collected within 48 hours post-mortem were organ cultured for 21 days in serum-free medium. An additional six pairs of corneas were cultured in medium containing serum for up to four weeks. The age of the donors ranged from 6 months to 80 years, but the majority were within the 18 to 80 year range.

One cornea from each pair was treated with the VisX Star 2020C excimer laser to create a wound of 6 mm diameter. The ablations performed were at −12.00 D using a single pass algorithm. This was a high myopic treatment that removed the epithelium and stroma to a depth of 180–190 $\mu$m.

Organ Culture

Figure 19A:
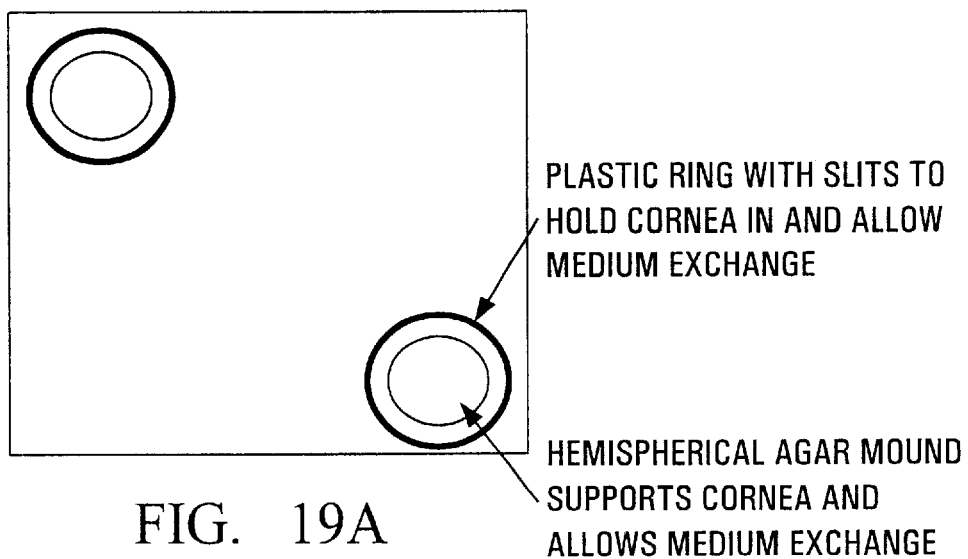
FIG. 19 is a diagram summarizing the organ culture protocol. A. View of culture dish assembly from the top. B. View of culture dish assembly from the side. C. Corneas in culture at an air-liquid interface, created by the up and down cycles of the rocker.

Two plastic rings were placed in diagonally opposing corneas of a square culture dish (FIG. 19A). If a round dish is used, the rings should be kept apart. Sterile melted wax was used to adhere the rings by the legs to the dishes. However, as mentioned above, corneas may be without the rings if they have sufficient scleral ring to stabilize them on top of the agar.

About 10 ml of melted liquid agar (a 2% agar w/v agar mixture in medium only was pre-made and stored in a Pyrex or other boiling resistant glass bottle at 4° C. When needed, the bottle was placed on a hot plate and the agar melted. The hot agar was then diluted with a 2×medium and was poured into each dish, making sure that the legs of the plastic rings were sealed in. Additional agar was pre-poured into the concave wells of depression dishes. These formed convex mounds that were placed within each plastic ring and sealed into place with melted agar. These formed the supports for the curved corneas and should conform to curvature of the cornea. (When rabbit corneas, which have a much greater curvature than human corneas, were organ cultured, we had to double up the mounds to support the cornea).

Figure 19B:
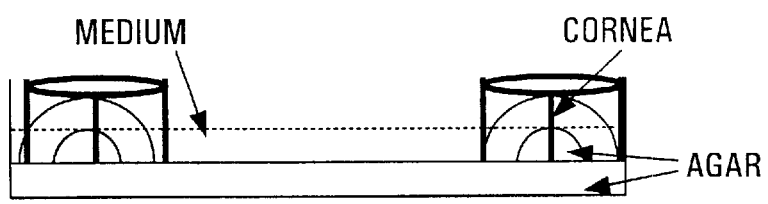
Figure 19C:
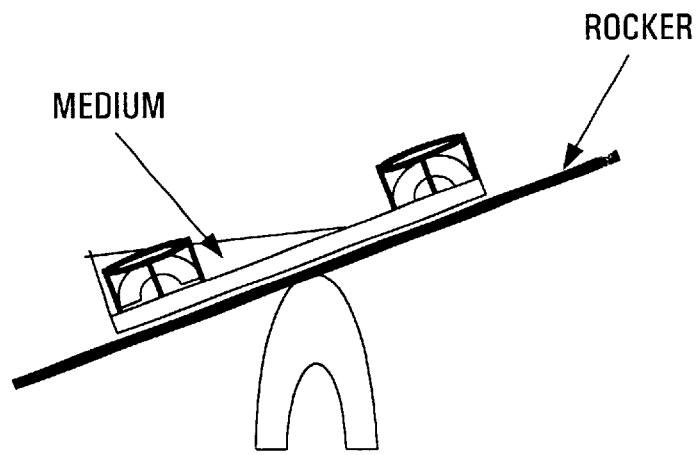

Medium was added to the culture plates just prior to use. The pairs of corneas were placed on the agar mounds at either end of the dish, with the endothelial surface resting on the agar (FIG. 19B). The dishes were labelled to distinguish between the two corneas. Each dish was then placed on a rocker (FIG. 19C) with an angle of 7 to 10° that would rock the dish at 10 cycles per minute (Richard et al. 1991). The amount of media used (8–12 ml) was just enough to cover one cornea at the down cycle. The cultures were maintained in a humidified environment at 37° C. with 5% $CO_2$ and 95% air. The rocking and intermittent flow of medium over the cornea simulates "blinking".

Corneal Evaluation

Corneas were bisected and fixed at times 0, 1, 5, 10 days and 3 weeks after PRK treatment. Half of each cornea was processed for paraffin embedding and H&E-stained for routine light microscopical histopathological examination. The other half was either dehydrated through an alcohol series, critical point-dried and sputter-coated for scanning electron microscopy (SEM) and then re-embedded for transmission electron microscopy (TEM); or directly processed for resin-embedding in Spurr's resin and TEM observation. SEM micrographs were taken on a JEOL JSM 6400 scanning electron microscope. For TEM, the resin-embedded samples were thin sectioned and stained with lead citrate for visualization with a Philips 420 transmission electron microscope.

Human corneas cultured as described showed uniformed stratified squamous epithelia of four to six layers for up to three weeks (FIG. 20A). We have found that corneas retrieved within 24 of death had 5–6 layers while the ones retrieved closer to 48 hours showed 4–5 layers. The endothelial layer was also intact (FIG. 19B). At four weeks, the epithelial layer was thinner, with only two to four layers. However, TEM micrographs showed that the cells had electron lucent nuclei, organelles, junctional complexes and characteristic microplicae (FIG. 20). Culture artifacts were present but the ultrastructural observations suggested that the cells were still healthy. The use of an antioxidant, such as superoxide dismutase and a protease inhibitor, such as aprotinin (Table 1) has allowed extension of the culture period of the corneas by about one week (from three to four weeks).

Figure 21A:
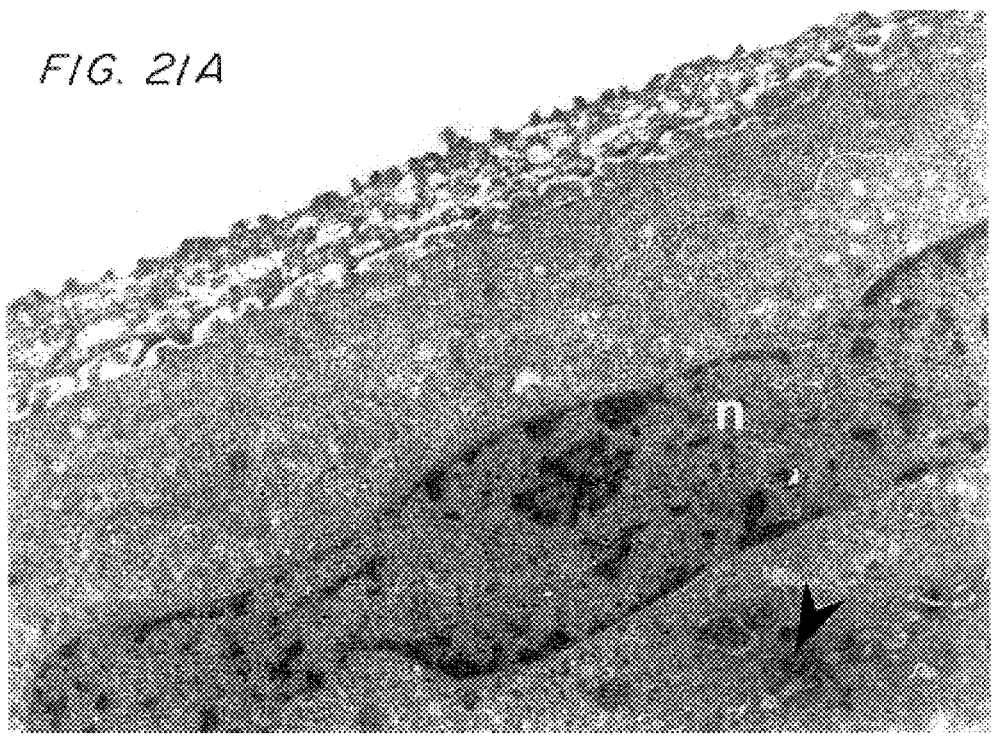
FIG. 21 are TEM micrographs of the corneal epithelium after 2 weeks in culture. A. Cell showing an electron lucent nucleus (n). B. Cells also retained their junctional complexes (arrowheads) and characteristic microplicae (m). Culture artifacts (*) were present but the ultrastructural observations suggested that the cells were still healthy.
Figure 21B:
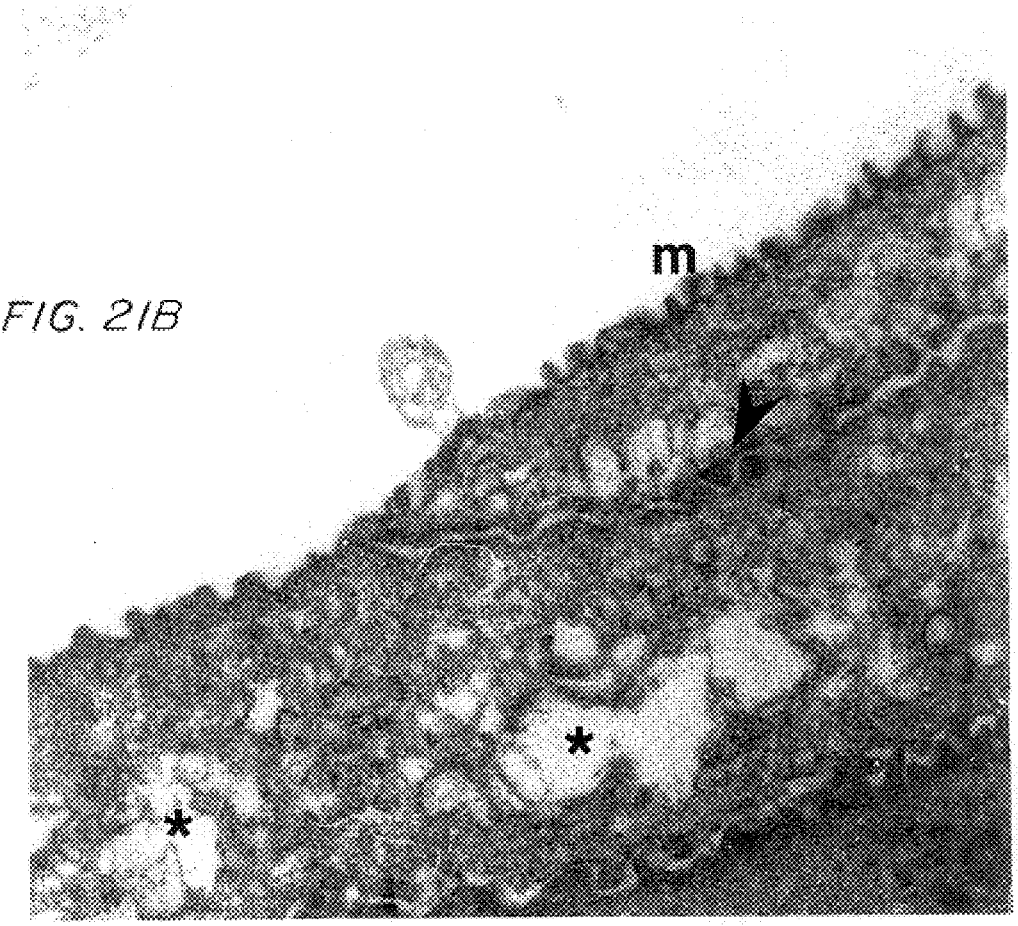

Corneas were treated to a depth of about 180–190 $\mu$m, which was over one-third the corneal thickness (cornea is about 500 $\mu$m in the central zone) showed healing in culture. SEM showed a smooth ablation surface after the procedure with no epithelial cells. By 5 days post-treatment, however, there was epithelial ingrowth. By 10 days, there was re-stratification (FIG. 21). Re-stratification occurred even in samples where the stroma showed edema. Edema within the stroma is frequently observed after deep laser ablations.

Figure 22:
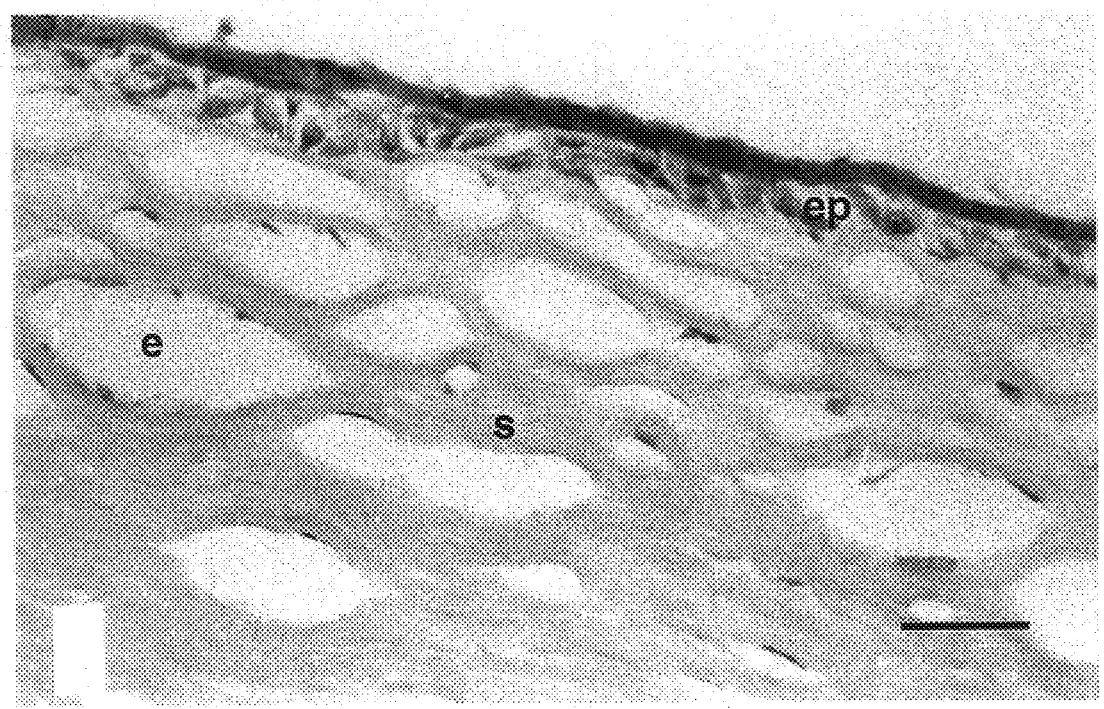
FIG. 22 is a section through a cornea that was ablated to give a wound of 6 mm in diameter and about 190 $\mu$m deep (cornea thickness is 500 $\mu$m) after 10 days in organ culture. The stroma (s) underlying the ablation in samples with such deep wounds often develops edema (e). However, the epithelium (ep) has grown over the stroma and there is some re-stratification. Bar, 20 $\mu$m.
Figure 23A:
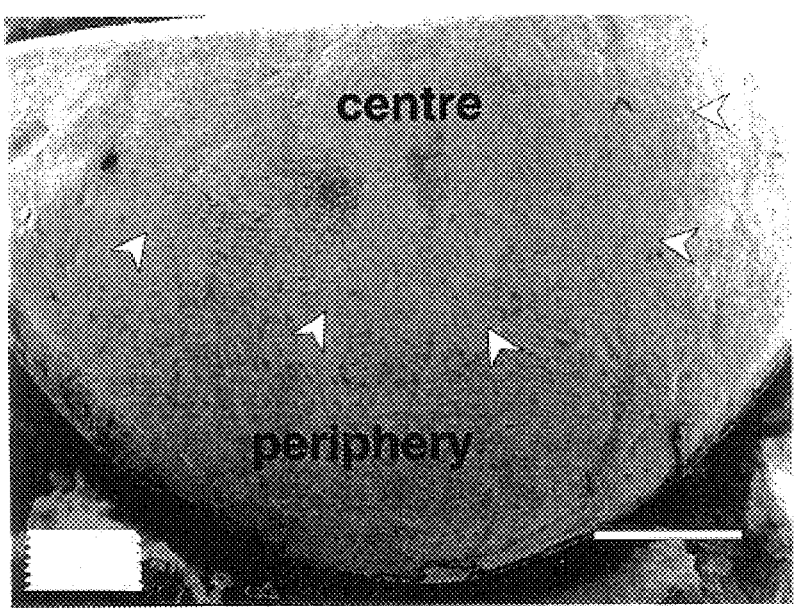
FIG. 23 are electon micrographs. A. SEM of half a cornea that had been treated with the excimer laser in the central zone. High myopia treatment parameters of 6 mm, –12 D (about 190 $\mu$m deep) were used. Arrows indicate the treatment boundary. Bar, 2 mm. B. Epithelial cells in the treated central area. Bar, 100 $\mu$m. C. Epithelium in the untreated peripheral area. Bar, 100 $\mu$m.
Figure 23B:
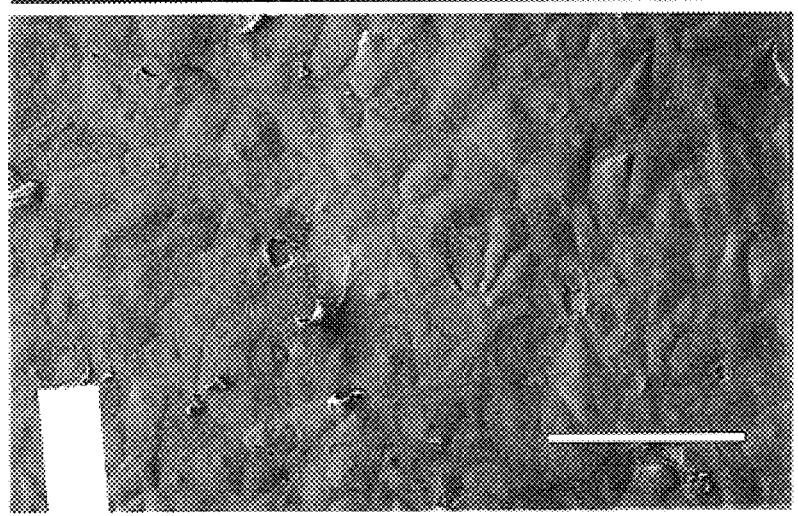
Figure 23C:
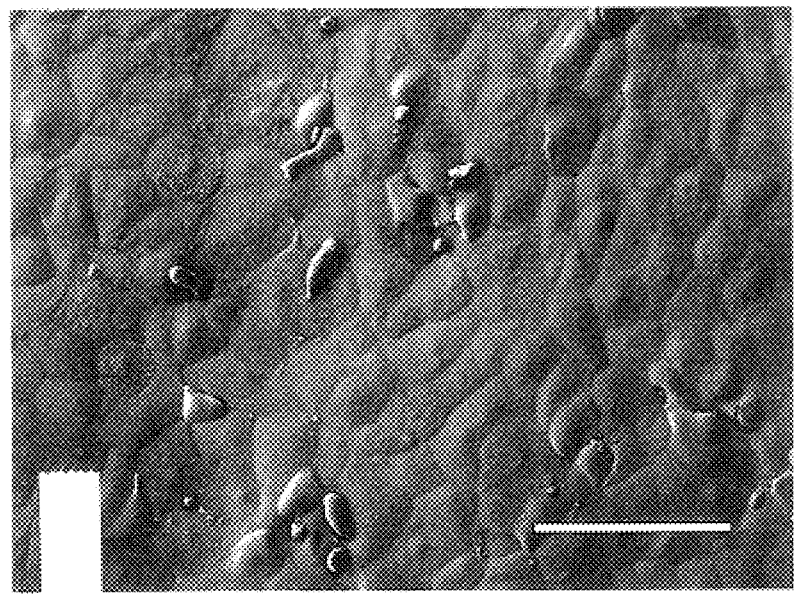

At 10 and 21 days post treatment, the epithelial surfaces were showing confluence and the treated areas were indistinguishable from the untreated regions (FIG. 22). These corneas were maintained in serum-free medium.

Organ culture of the human cornea is used in research and, in Europe, as a means of extending the lifespan of the human cornea for transplantation purposes, after the death of the donor. The traditional submerged culture method of maintaining corneas has several drawbacks, such as the thinning of the epithelium, development of edema within the stroma and subsequent swelling. These changes in the cornea makes it difficult to correlate the results of in vitro experimental procedures on the corneas, with the actual in vivo situation due to the distortion of the cornea.

The first reported major breakthrough in the organ culture of human corneas was the work of Richards et al. (1991). These investigators cultured human corneas at an air-liquid interface. This eliminates the culture artifacts of the submerged culture system.

The use of the air-liquid interface culture system has also shown superior results compared to the submerged culture systems and, in the main, has worked for other organs. Palates have been successfully cultured from mouse embryos and fused in vitro, and have been found to undergo osteogenesis in the presence of a 50% oxygen, 5% carbon dioxide and 45% nitrogen gas mixture (Griffith and Hay, 1992). Palates grown in submerged systems developed cartilage, presumably due to the lower oxygen content in the medium. Culture artifacts and some swelling were also present.

The present application describes a simple method for obtaining consistent results in the organ culture of whole corneas. A 1% agar-medium gel was used to support the cornea while providing an environment for constant nutrient-metabolic product exchange through the endothelial layer, even when the epithelium is completely exposed to air during an up-cycle on the rocker. The use of the agar support eliminates the possibility of endothelial exposure to air, and mimics the aqueous and vitreous humor of the eye. The serum-free defined medium permits control of experimental conditions. The elimination of serum eliminates the presence of unknown serum proteins such as cytokines that will have effects on wound healing. The various components of the serum-free medium, including an antioxidant and a protease inhibitor, allow the healing of deep wounds to more than one-third the thickness of the cornea (as caused in this study by ablation with the excimer laser). The re-epithelialized surface was morphologically similar to untreated surfaces.

The use of serum-free medium allows for more complete characterization of the experiemental conditions. Furthermore, the use of a semi-solid gel support allows constant exchange of nutrients, metabolic products during the entire culture period and hence provides consistently good culture results. The present system was able to maintain the corneas as well as allow for the healing of deep corneal stromal wounds. This model can also be used for the study of the modulation of corneal stromal healing.

Vascular Endothelial Cell Lines

Human umbilical vein endothelial cells (HUVECs) were harvested from umbilical cord veins as previously described (Sirois E, et al., Int. J. Artificial Organs 16:609–619, 1993). They were grown on a gelatin-coated dish until confluence in Medium 199 supplemented with 20% FBS, 90 mg/l of heparin, 2 mM of L-glutamine and 100 $\mu$g/ml endothelial cell growth supplement (ECGS). Penicillin (100 I.U./ml), streptomycin sulfate (100 $\mu$g/ml) and amphotericin B (0.25 $\mu$g/ml) were present in medium. After the first passage, FBS concentration was reduced to 10% and ECGS to 20 $\mu$g/ml. Cells were subcultured at a ratio of 1:3 or 1:4 and HUVECs from the 2nd to 4th passages were used in our bioassays. Endothelial cell phenotype was verified by the diI-acetylated low-density lipoprotein (diI-Ac-LDL) uptake and positivity to factor VIII-related antigen antibodies by immunocytochemistry. Cultures were incubated in 5% $CO_2$ atmosphere at 37° C. in saturated humidity. The medium was changed every other day.

For transfection, primary HUVECs were seeded onto uncoated 60 mm tissue culture plates and cultured until 60–70% confluent. They were then immortalized by infection with the HPV16 E6 and E7 genes and selected by G418 resistance as described above.

Figure 16:
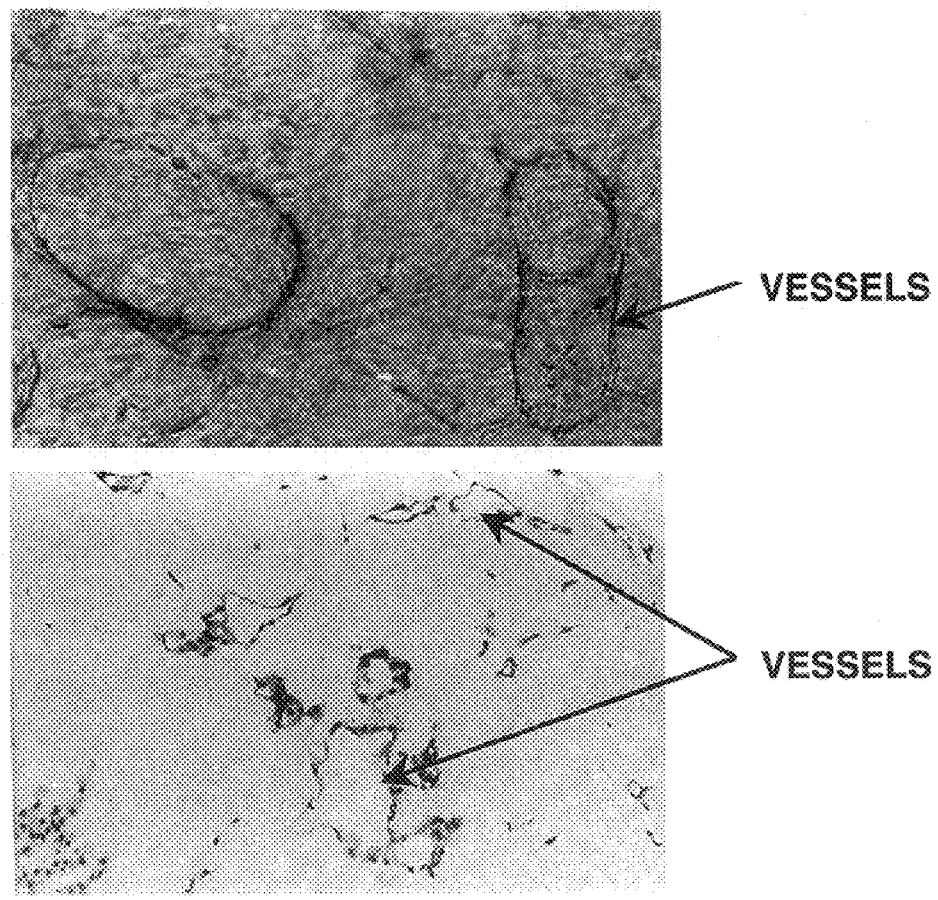
FIG. 16 shows immortalized vascular endothelial cells in fibrin matrix after 4 days of cell culture in serum-free medium. A. In phase contrast, microvessels can be distinctively seen forming a network within the whole thickness of the matrix. Mag. 36×. B. On histological sections, capillary-like vessels can be observed. Mag. 90×.
Figure 17:
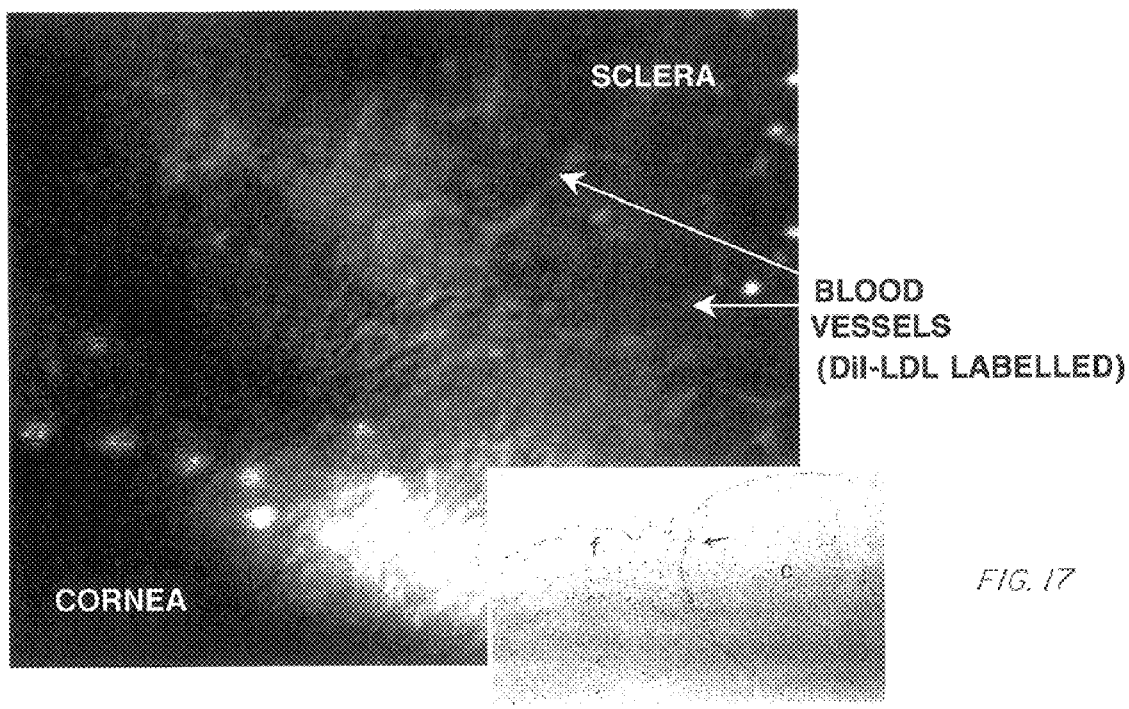
FIG. 17 shows reconstructed human cornea and sclera. The angiogenic cells of the sclera have been labelled with a fluorescent marker, DiI-conjugated Low Density Lipoprotein (DiI-LDL). Inset: H&E-stained cornea and sclera. f, fibrin matrix with blood vessels; c, cornea. The cornea-sclera junction is indicated by the arrow.
Figure 18:
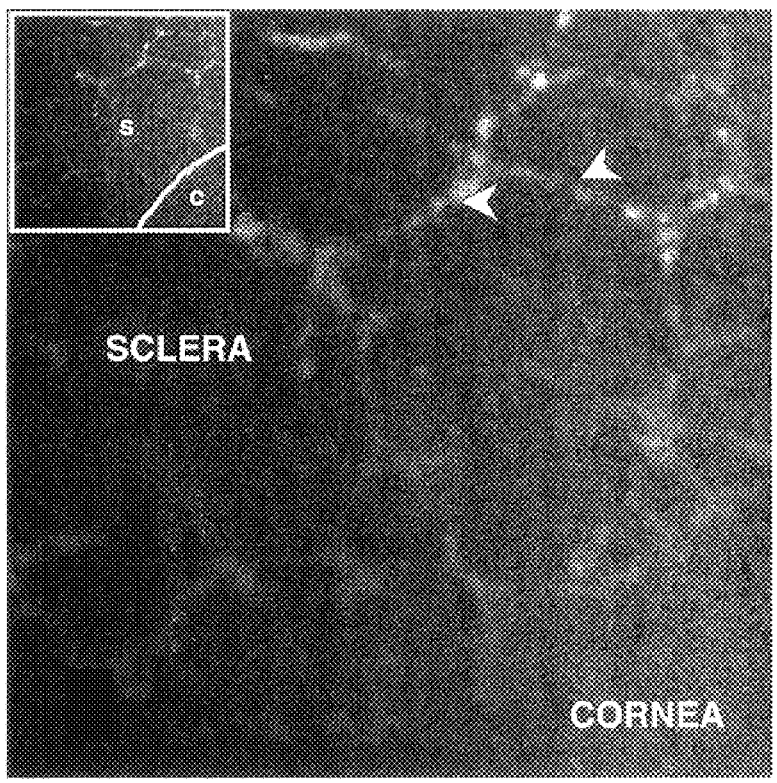
FIG. 18 shows higher magnification of the sclera showing Di-I-LDL labelled blood vessels.

The virally transfected HUVECs were tested for functionality by their ability to undergo angiogenesis in a three-dimensional fibrin-containing matrix (FIG. 16); and their ability to sequester acetylated low density lipoprotein labelled with 1,1'-dioctadecyl-3,3,3',3'-tetramethylindocarbocyanine perchlorate (DiI-Ac-LDL; Biomed. Technol. Inc., Stoughton, Mass.), (FIGS. 17 and 18). Immortalized HUVECs can also be maintained in the serum-free medium. Similarities and differences between primary and immortalized HUVECs are summarized in Table 2. As with corneal cell lines, other genes can also be introduced into HUVEC lines. For example, GFP has been introduced by transfection.

TABLE 2

Summary of similarities and differences between primary and immortalized HUVECs.

| Medium Conditions | Days | Methods | Normal Cells | Cell Lines |
|---|---|---|---|---|
| Cell Phenotype | | | | |
| | | DiL-Acetyl-LDL uptake | + | + |
| | | Factor VIII (immunocytochemistry) | + | + |
| Angiogenesis assay in fibrin | | | | |
| | 7 | | cord-like structures | tubes and capillary-like structures (50–250 $\mu$m height) |
| | 15 | | tubes and capillary-like structures (50–100 $\mu$m height) | tubes and capillary-like structures (50–250 $\mu$m height) + lysis |
| | 21 | | tubes and capillary-like structures (200–500 $\mu$m height) | Nil |
| Endothelial Cell Migration (from collagen gel to fibrin gel) | | | | |
| | 7 | | none | +++ |
| | 15 | | + | ++++ |
| Response to Growth Factors | | | | |
| FGF-2 (50 ng/ml) | | | Angiogenesis | Angiogenesis |
| FGF-2 | | | Cell death | Cell death |

Reconstruction of the Cornea and Sclera

The cornea complete with a surrounding sclera can be reconstructed in a variety of ways, using a range of cellular concentrations. Described below are two methods that have been optimised:

Method 1

Figure 2A:
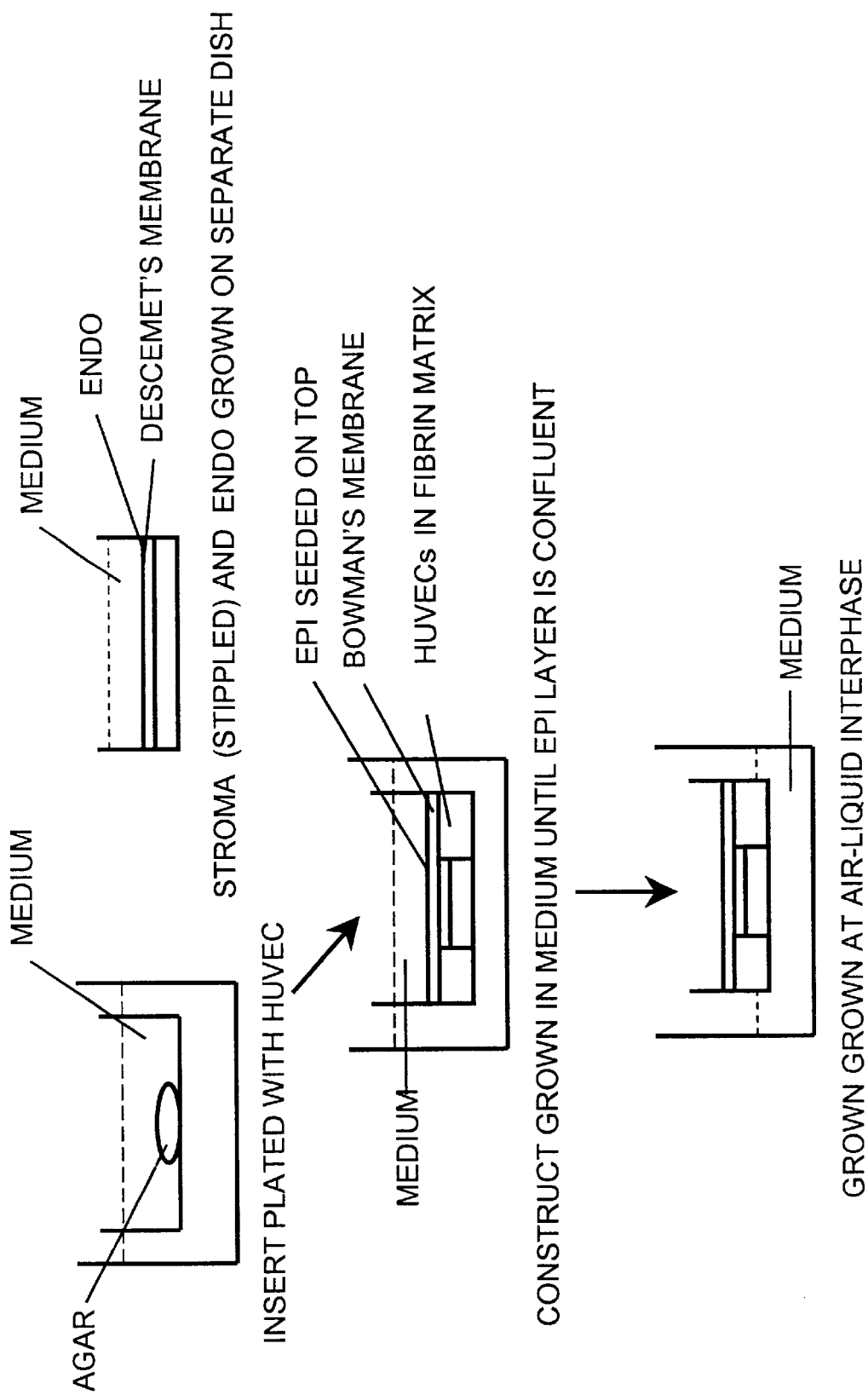
FIG. 2a shows one method used in reconstruction of the cornea and sclera in vitro.

(Summarized in FIG. 2a)

As for the cornea alone, preferably either Costar transwell inserts that are pre-coated with type I and type III collagen, or collagen-coated Milllicell-CM (Millipore) culture inserts were used. A circular piece of agar or fibrin. gel was placed in the centre of the culture insert and HUVECs were seeded at a density of $5 \times 10^4$ cells per ml and allowed to grow to confluence, supplemented by culture medium that had 0.09 g/l heparin, 0.02 mg/ml endothelial cell growth supplement (ECGS, Becton Dickinson).

Stromal and endothelial samples were simultaneously prepared and timed to have contracted at the same time as the HUVECs reach confluence. Stromal samples comprise keratocytes embedded in a collagen-chondroitin sulphate matrix as described previously. Retinol acetate was added to the stromal matrix to prevent contraction of the gel. Descemet's membrane was laid down on top of the stromal matrix and endothelial cells were seeded onto this membrane at $10^3$ cells/ml. When the HUVECs attained confluence, the agar or fibrin gel was removed and the stroma and endothelial compartments were placed in the centre of the dish with the endothelial cells at the bottom.

The sclera, which was a combination of $10^5$ to $10^7$ vascular endothelial cells in a 0.3% to 1% fibrinogen (optimal is 0.3%) (fraction I; type I-S from bovine plasma (human fibrinogen can also be substituted)), 0.2%–1% (optimal is 0.25%) gelatin matrix, polymerized by addition of thrombin (various doses can be used, higher doses give a firmer gel) was then poured around the stroma and allowed to set. Bowman's membrane was then layered on top as described above and finally, epithelial cells were seeded on top of Bowman's membrane.

Method 2

Figure 2B:
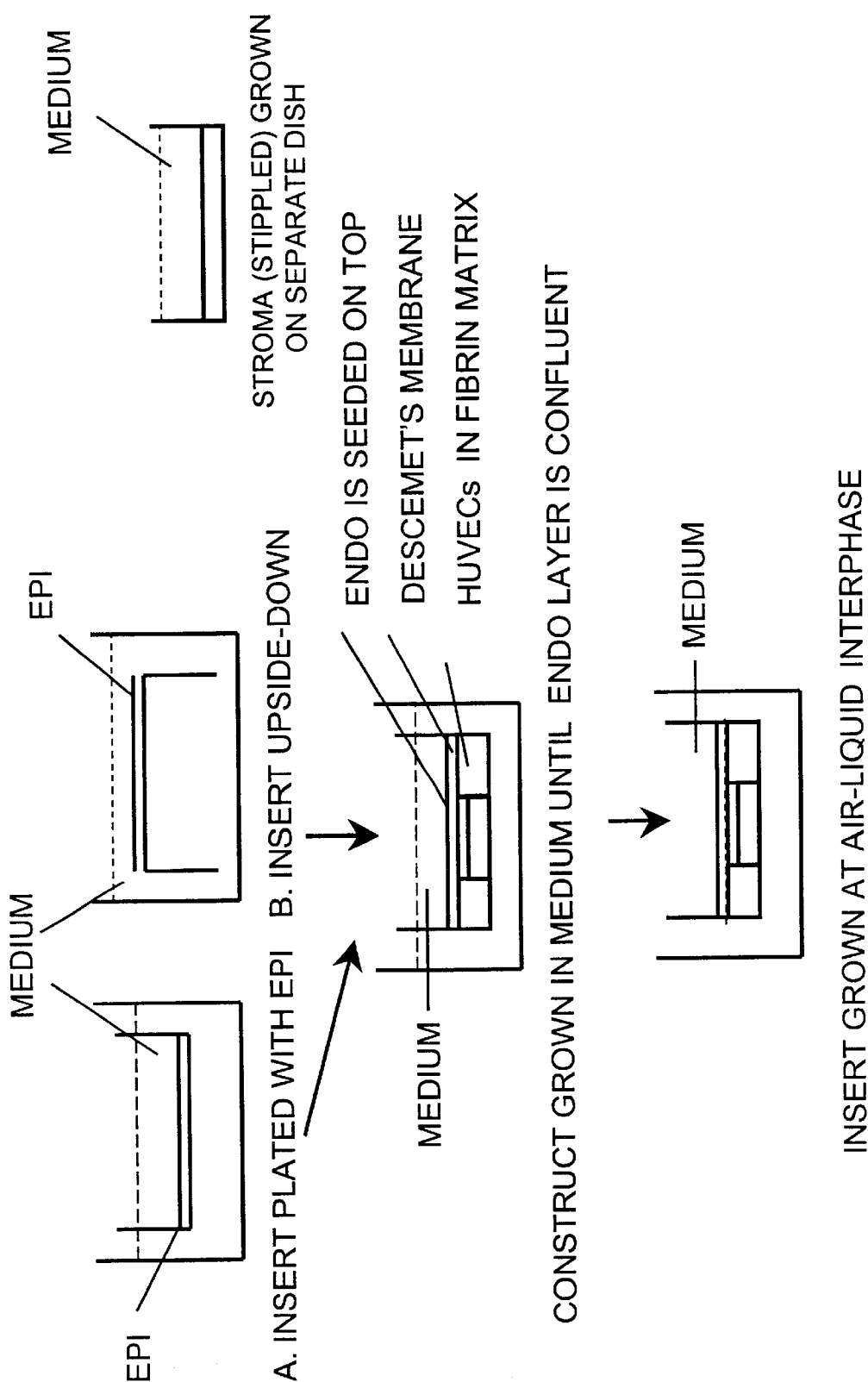
FIG. 2b shows another method of reconstructing the cornea and sclera in vitro.
Figure 3:
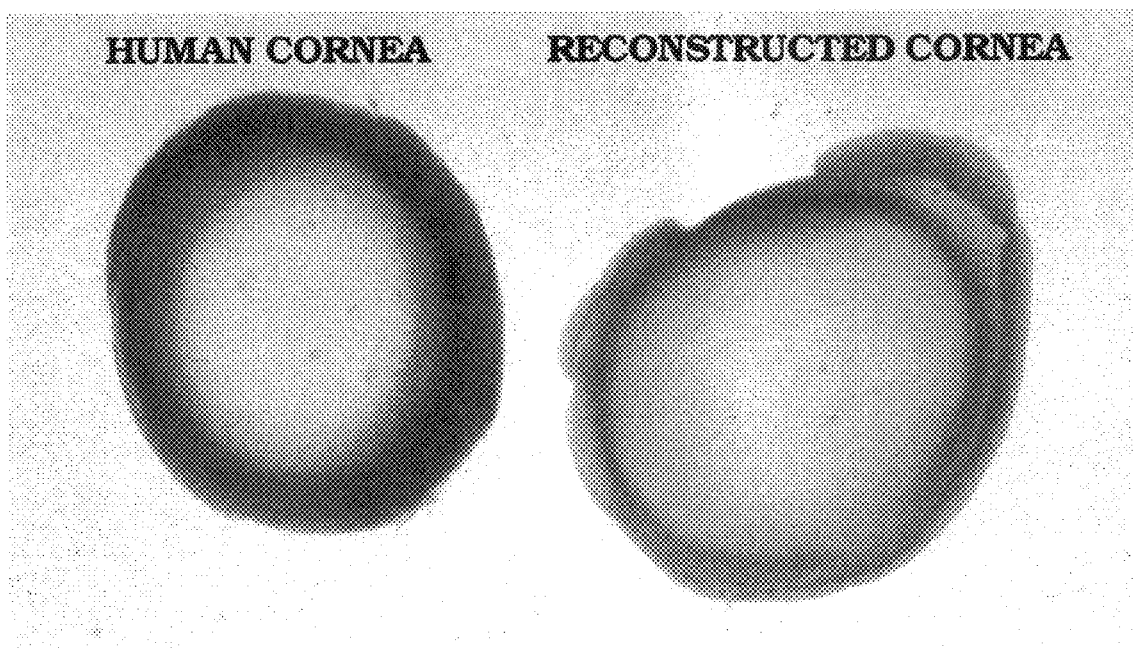
FIG. 3 shows human cornea obtained from the Eye Bank and a cornea that was reconstructed from cell lines. Both were organs cultured in serum-free medium for one week.
Figure 4:
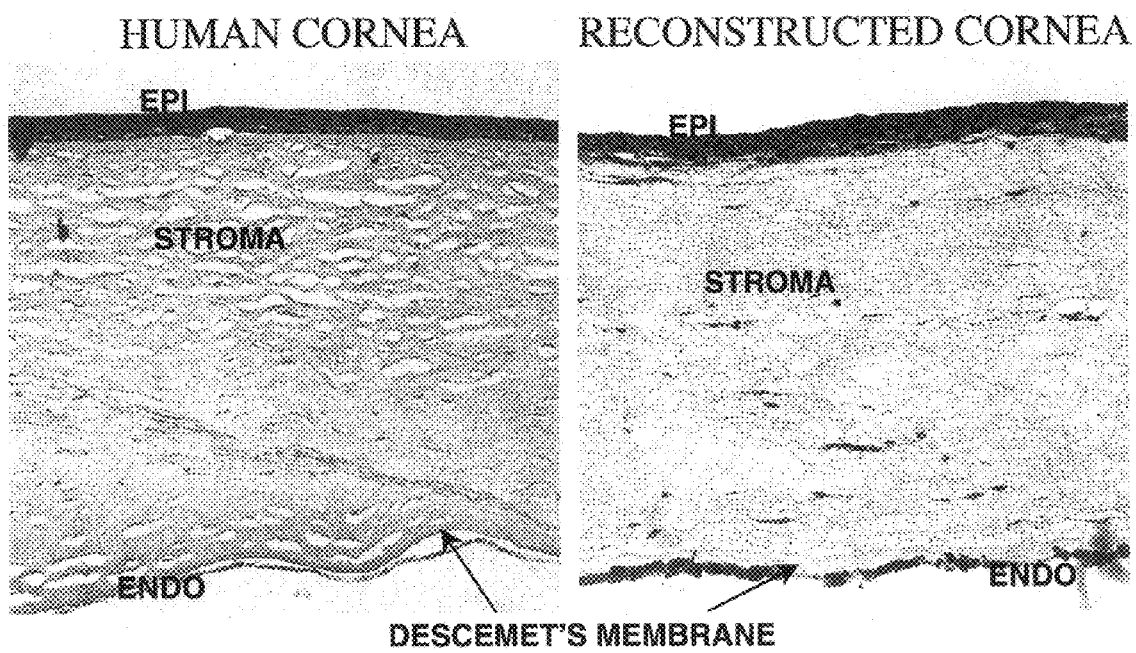
FIG. 4 shows sections through a reconstructed cornea compared with an organ-cultured human cornea. Both show well defined epithelial, stromal and endothelial layers. Descemet's membrane is present in both specimens. However, Bowman's layer is not prominent in either specimen as seen in other samples of organ cultured human corneas.
Figure 5:
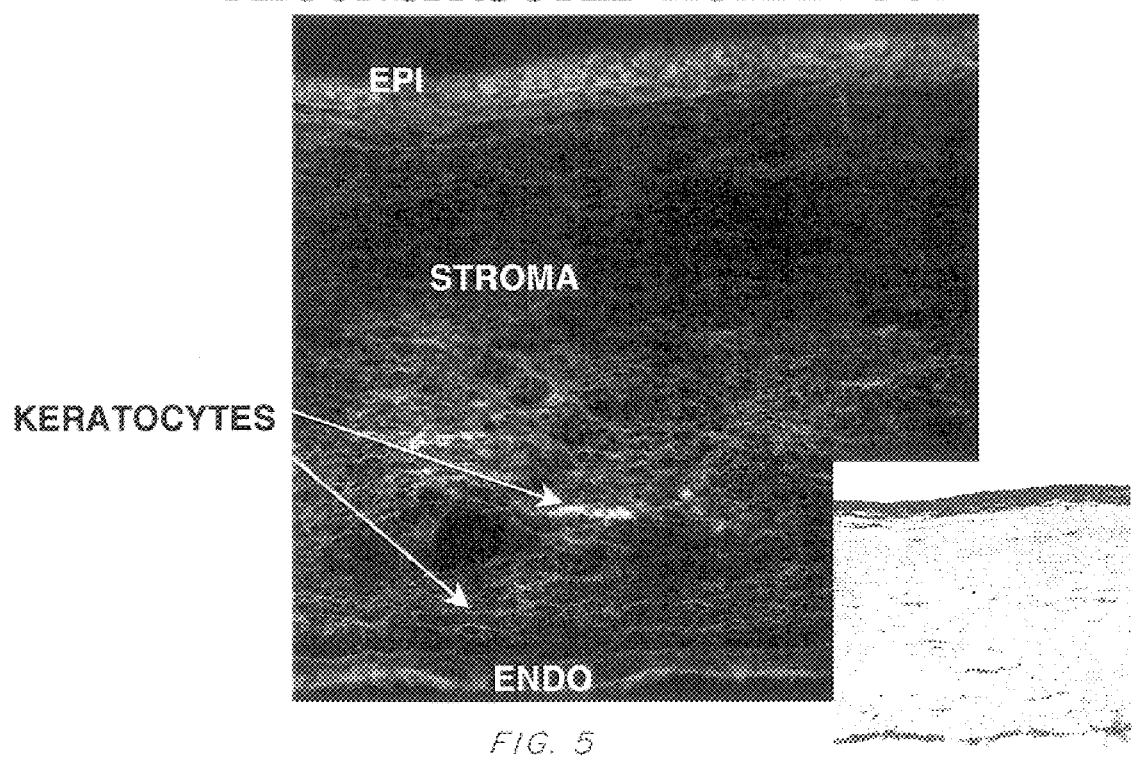
FIG. 5 shows a section through a reconstructed human cornea visualized with epilfluorescence by confocalmicroscopy. The epithelial and endothelial layers are distinct, and keratocytes are present in the collagenous stromal matrix. Inset: H&E-stained section of the same cornea.
Figure 6:
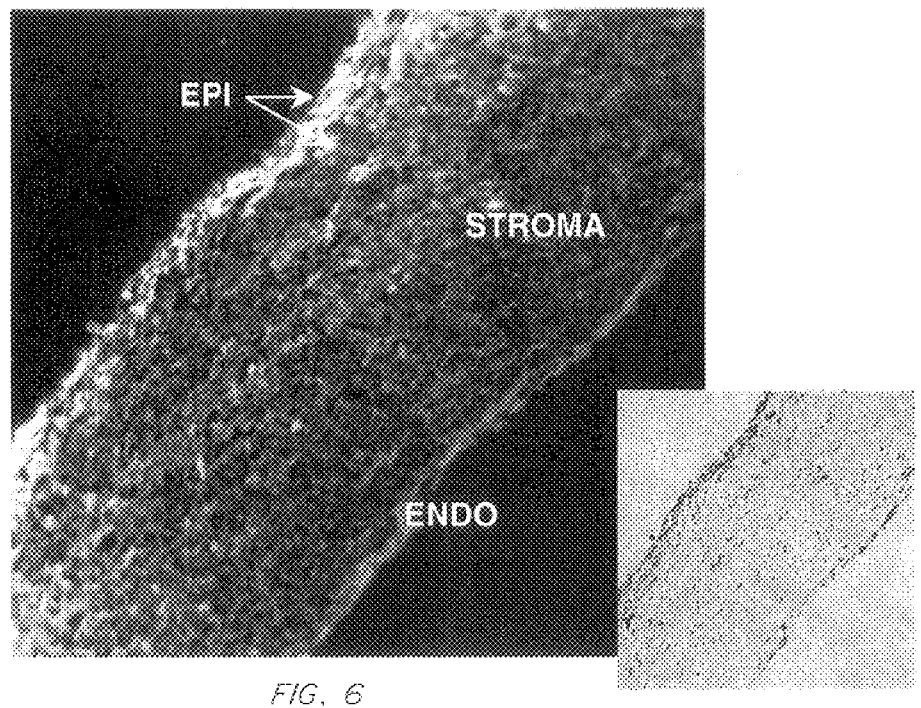
FIG. 6 shows a cornea that was reconstructed with cell lines that were transformed. The three main layers are not readily distinguishable and the transformed epithelial cells are seen invading the stromal compartment. This sample demonstrates the importance of obtaining immortalized cell lines that are physiologically similar to low passage primary cells from the human cornea. Inset: H&E-stained section.
Figure 7:
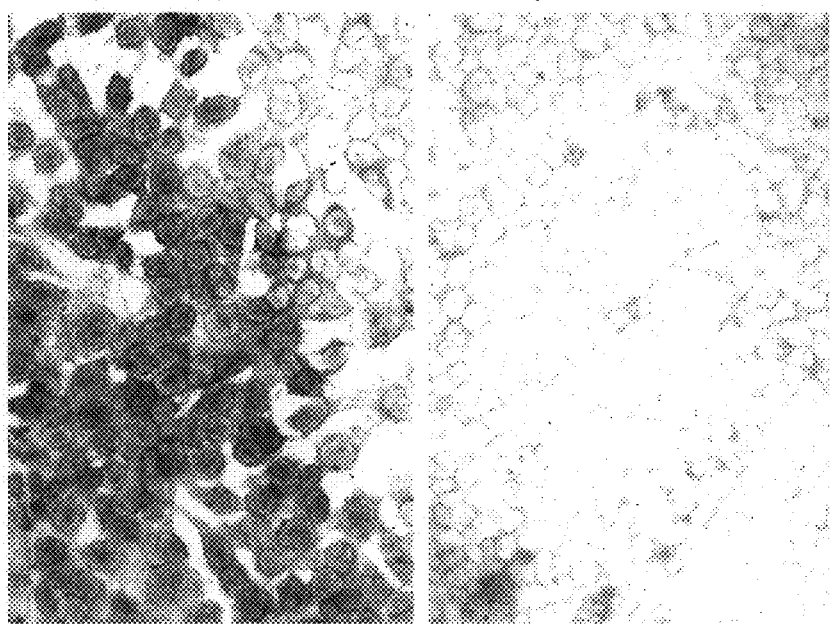
FIG. 7 shows in situ hybridization, using a probe for alpha2 (VIII) collagen, which is found in Descemet's membrane in the cornea and is known to be produced by corneal endothelial cells. Alpha2 (VIII) mRNA is produced by this endothelial cell line, as shown by visualization of cell-bound alkaline phosphatase conjugated DIG-antisense riboprobe. The sense control-probe cells remain unlabelled.
Figure 8:
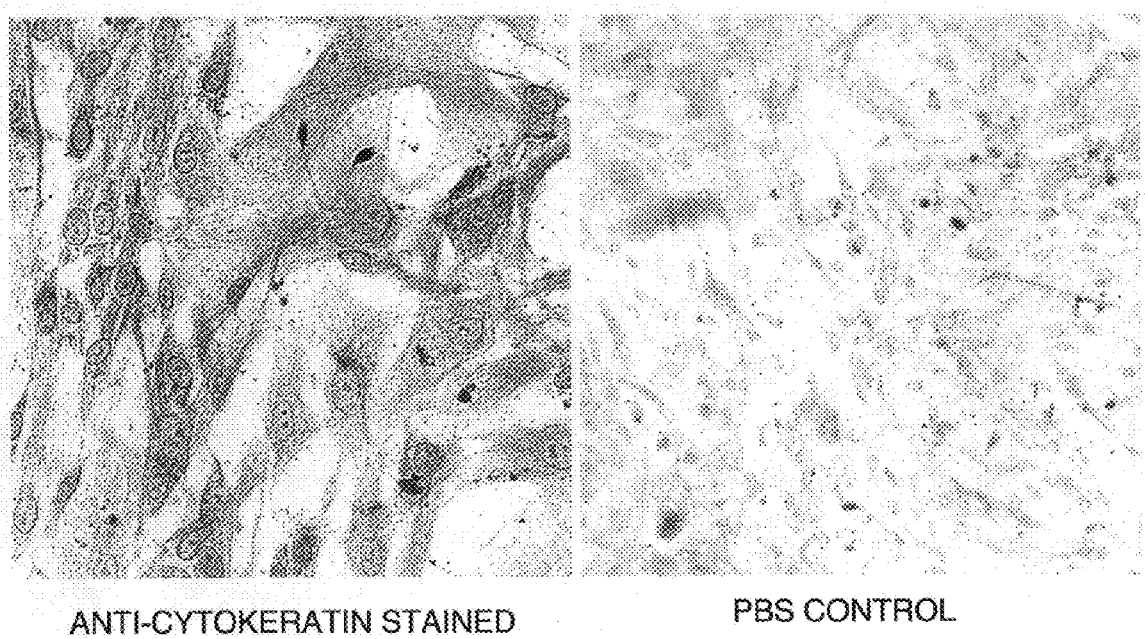
FIG. 8 shows an epithelial cell line showing expression of a standard marker, cytokeratin by immunohistochemistry.
Figure 9:
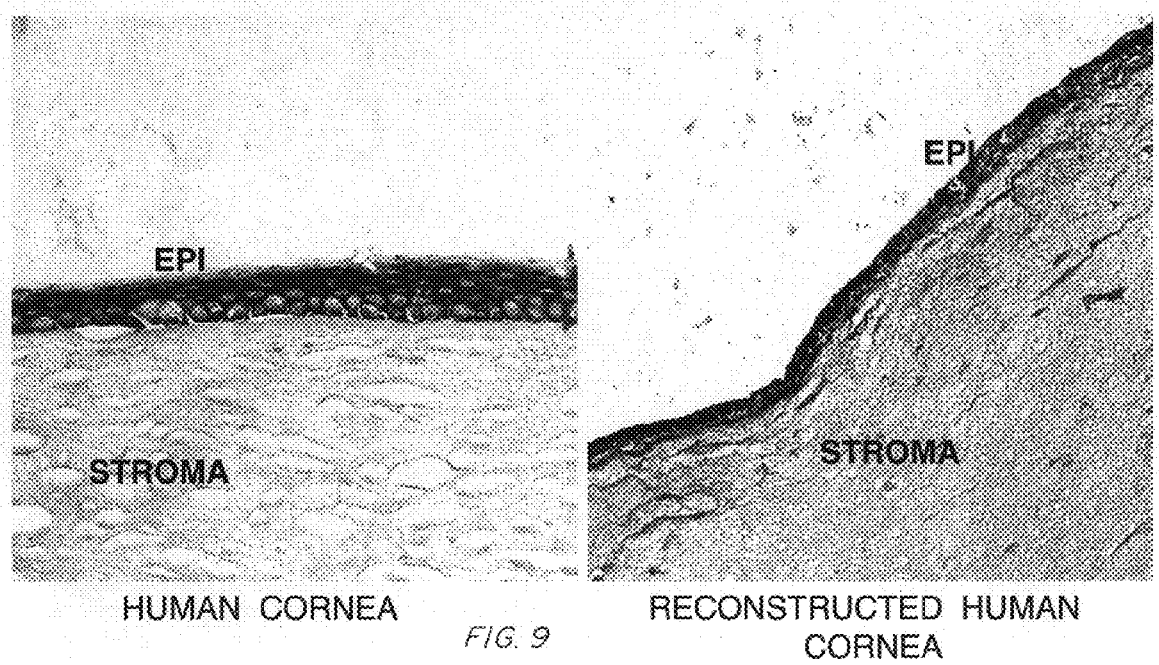
FIG. 9 shows cytokeratin expression in the epithelium of a human cornea and in a reconstructed cornea.
Figure 10:
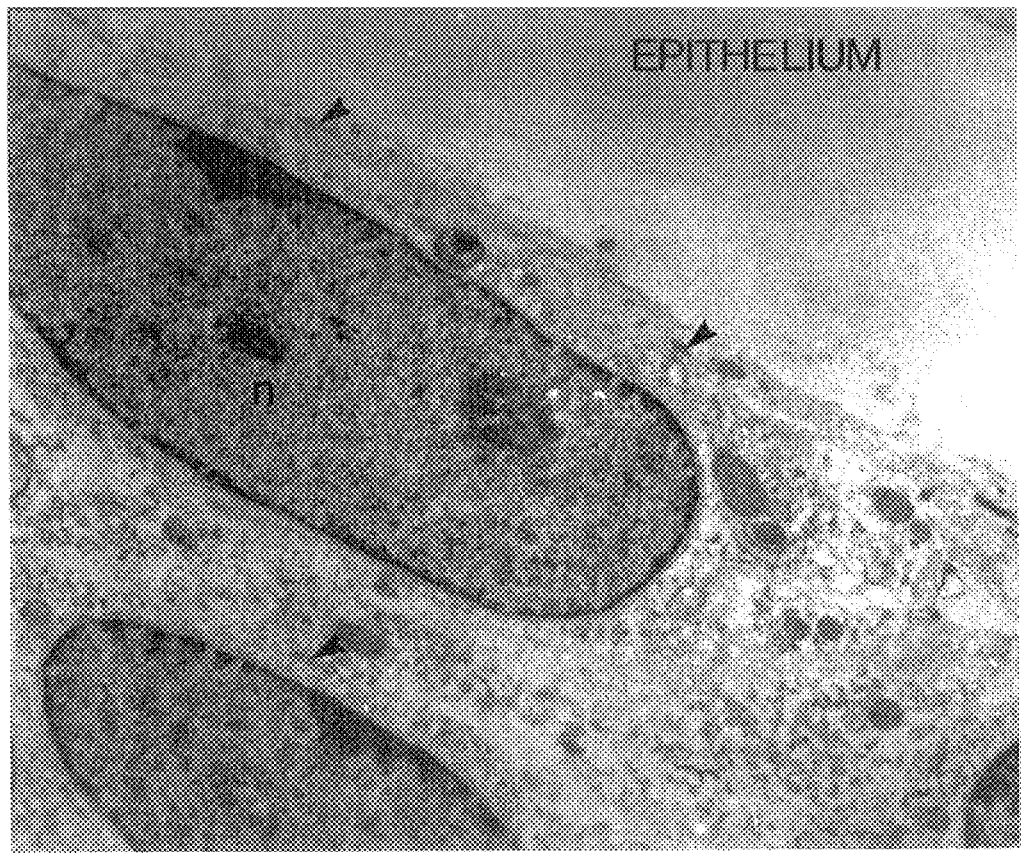
FIG. 10 shows a transmission electron micrograph of the epithelium of a reconstructed cornea after two weeks of culture at an air-liquid interface. Microplicae, a characteristic of corneal epithelial cells are present on the external surface and junctional complexes have formed between cells (arrowheads).
Figure 11:
FIG. 11 shows a transmission electron micrograph of a reconstructed cornea after two weeks of culture at air-liquid interface, showing stromal keratocytes within a largely collagenous matrix. The nuclei (n) are electron lucent, and there are mitochondria (arrowheads) in the cytoplasm, indicating that the cells are healthy.
Figure 12:
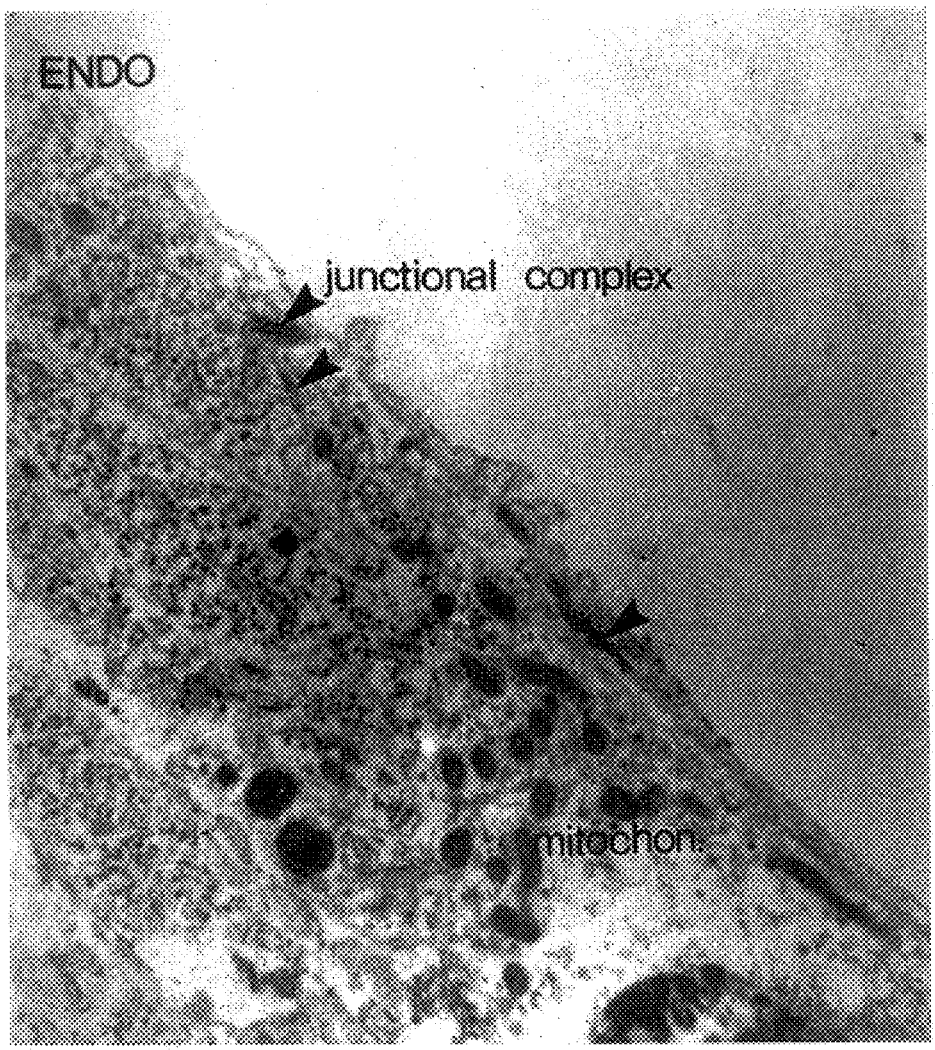
FIG. 12 shows a transmission electron micrograph of the endothelial layer of a reconstructed cornea after two weeks of culture at air-liquid interface. Mitochondria are present in the cytoplasm as indicated, and junctional complexes (arrowheads) have formed between cells.
Figure 13:
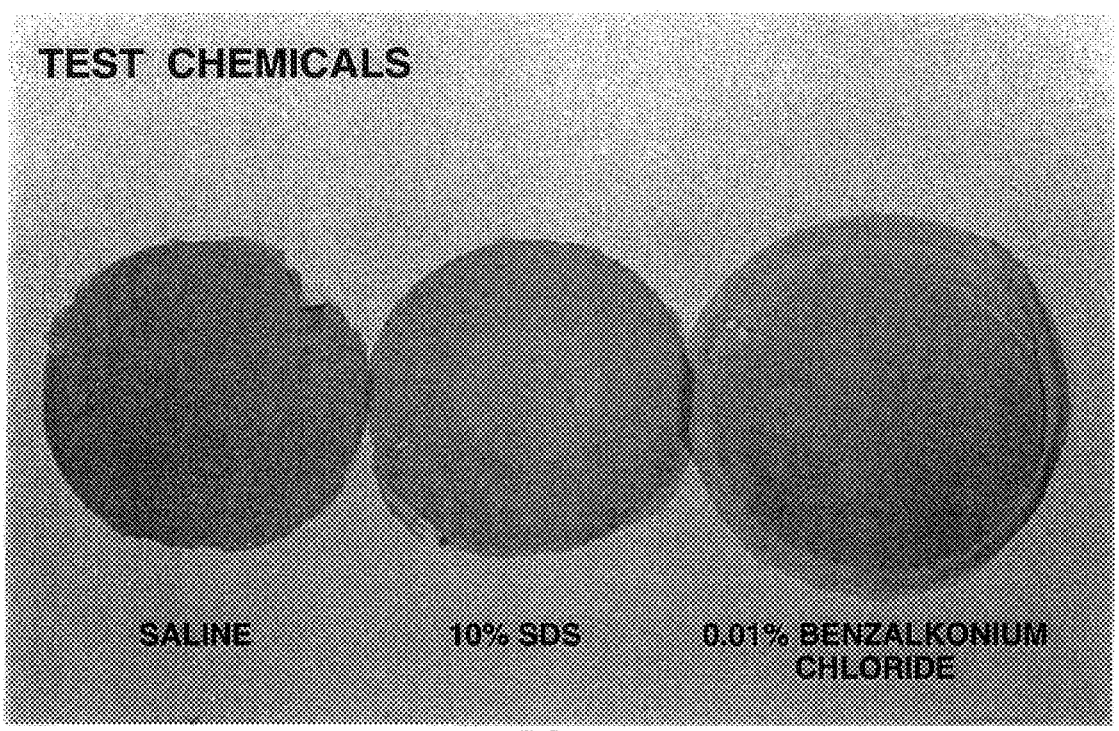
FIG. 13 shows responses of reconstructed corneas to different aqueous test chemicals. Each cornea was exposed centrally to 100 $\mu$l of the test chemical for 10 min, after which the chemical was washed off with saline and the corneas were re-cultured for a further 3 days. The saline-treated cornea served as the control. Treatment with 10% SDS and the dilute benzalkonium chloride solution caused wounds to the centre of the cornea as seen in changes of corneal transparency. The wound caused by the 0.01% benzalkonium chloride solution was able to heal but the SDS wound is still unhealed.
Figures 14A, 14B:
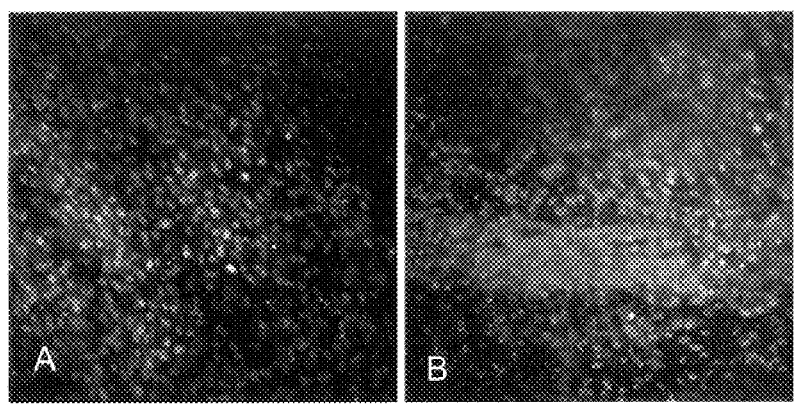
FIG. 14 shows differences in responses of reconstructed corneas to SDS and 0.01% benzalkonium chloride solution, as visualised by live-dead staining. Live cells are green, while dying or dead cells are orange-red. A. Epithelial cells of dilute benzalkonium chloride treated cornea, showing some dead and dying cells but mostly live cells. B. SDS-treated construct, showing mostly dead and dying cells. C. Stromal cells of the benzalkonium solution-treated cornea are mostly alive, showing little/no penetration of solution into the stromal compartment. D. Stroma of SDS-treated cornea showing orange-red dead or dying cells, indicating penetration of the detergent into the stroma.
Figures 14C, 14D:
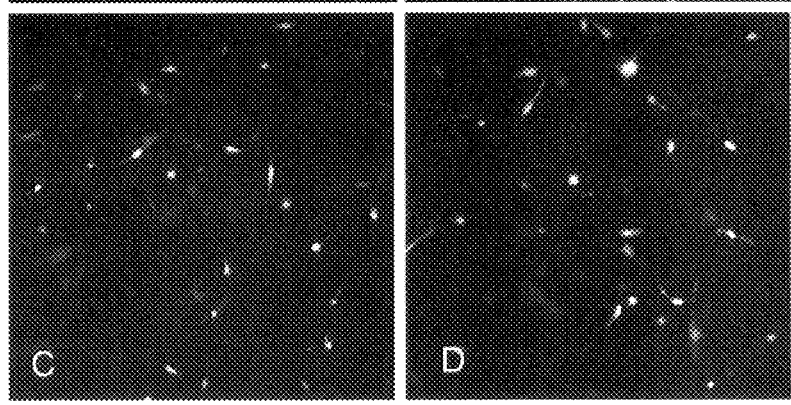
Figure 15:
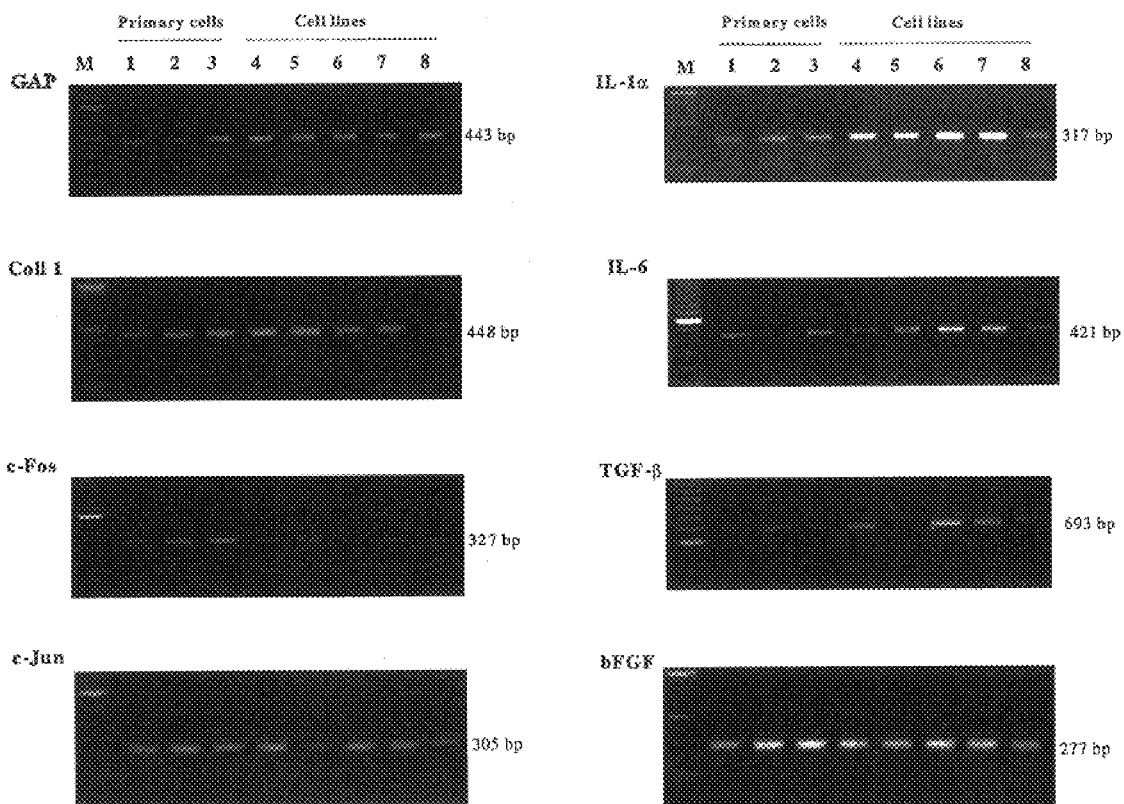
FIG. 15 shows RT-PCR products showing expression of mRNA for 8 genes that have been found to be related to corneal functioning, particularly in wound healing. Baseline levels in primary cultures of human corneal cells are compared with the immortalized cell lines that we have established. mRNAs for GAPDH (control housekeeping gene), Coll 1, c-fos, c-jun and bFGF are expressed equally in all the 8 types of cells. IL-1a mRNA appears to be expressed at a higher level (or a similar level) in epithelial and stroma cell lines than in the primary cells. IL-6 mRNA may be expressed at a lower level in the endothelial cell line than in the primary endothelial cells. 1=primary epithelium; 2=primary stroma; 3=primary endothelium; 4, 5=immortalized epithelial lines; 6, 7=immortalized stromal lines; 8=immortalized endothelial line.

(Summarized in FIG. 2b)

Epithelial cells are plated on a collagen coated insert and grown until confluence is achieved. Inserts can also be coated with 0.3% fibrinogen to allow for epithelial stratification. A Bowman's membrane is then applied on the epithelial layer. The insert membrane can also be used as a "pseudo-Bowman's membrane" by infiltrating with collagen and seeding the epithelial cells onto the underside of an inverted insert (FIG. 2b) and growing the cells until confluence, after which the insert is returned to its regular position. The stroma which had been fabricated separately as described in "Method One" is placed on top of the epithelial layer and surrounded with HUVEC cells ($10^5$ to $10^7$ cells/ml matrix) in the fibrinogen matrix. Descemet's membrane is layered on top of the stroma and HUVEC/fibrinogen matrix. Endothelial cells are then seeded on top. The inside of the insert is then supplemented with medium while the epithelial layer is left to grow at a liquid-air interface. This method reduces the culture time by up to one week (or the time required for the epithelial cells to achieve confluence on top of "Bowman's membrane").

During the assays in matrices, cells were grown in serum (10%) supplemented-medium 199 containing heparin, L-glutamine or modified glutamine such as L-Alanyl-L-Glutamine (GlutaMAX™, GIBCO) and antibiotics at the same concentration as described above, without ECGS, but with 50 ng/ml of FGF-2. Serum-free medium has also been used.

Reconstruction Protocol with Epithelium Down

Steps are reversed for constructs that have endothelium at the bottom of the insert and epithelium, polyethylene glycol (PEG) is laid down between the stroma and underlying layer (epi or endo) to prevent downward cell invasion).

All components are either purchased sterile or sterilized (eg. with a 0.2 µm filter). A base medium, such as M199 or DMEM (no phenol red) with serum or serum-free, is used.

Epithelium

Biocoat™ (Becton-Dickinson) collagen-coated 30 mm inserts or collagen-coated Falcon or Millipore-CM inserts may be used. Inserts can also be coated with 0.3% fibrinogen.

Epithelial cells are trypsinised and spun down, followed by resuspension in 0.5 ml of medium. Cells are then counted, e.g. with a haemocytometer.

Inserts are then seeded with about 5 to $7.5 \times 10^4$ cells/insert.

The inserts are supplemented with 2 ml of medium inside the insert, as well as on the outside.

Cells are then grown until confluence is reached.

Bowman's Membrane

After epithelial cells have reached confluence, the matrix is prepared as follows by mixing together gently but well (avoid forming bubbles) collagen, Type I, bovine dermal (3.3 mg/ml; 6 ml) and collagen buffer, 10× (see below; 0.6 ml). The resulting mixture is neutralised with 1 N NaOH, if needed.

Then, 100 µl fibronectin (1 mg/ml stock) is added and the resulting solution mixed well. All medium is then aspirated from the epithelium within the insert. The Bowman's membrane is layered on and allow to set. The inserts should not be moved during the setting process.

Once the Bowman's membrane has set (or preferably, just before it is completely set), PEG is layered on as follows. 10% PEG in medium only is added on top of Bowman's membrane. It is then left to sit for 30 min–1 hour in an incubator to form a thin coating over the Bowman's membrane. The solution is aspirated off completely just before adding the stroma. It has been possible to incorporate the PEG into Bowman's membrane directly, instead of this additional step.

Stroma

The following components are mixed together in the stated order, mixing gently but very well at each step:

Type I collagen (bovine dermal, approx. 3 mg/ml; 6 ml), collagen buffer, 10× (see below; 1 ml), chondroitin sulphate C (20% in PBS; 520 µL) and retinol acetate (5 mM; 12 µL).

To the above mixture, 100 µL of 1% glutaraldehyde in 20% dextran in medium (M199 or DMEM) is added and mixed thoroughly. The mixture is then left to cross-link at room temperature for at least 30 min to 1 hour, taking care that it is not allowed to solidify.

Unreacted glutaraldehyde is bound up and rendered 'non-toxic' by adding 450 to 500 µL of 20% glycine in medium, mixing thoroughly and letting the mixture react for at least 30 min. at room temperature. The mixture is neutralised with 1 N NaOH if required. The mixture is then further mixed with 5 to $7.5 \times 10^4$ cells/ml. 1.5. ml of the resulting solution is added to each insert. The inserts are then returned to the incubator until the collagen sets. If the stroma is prepared towards the end of the working day, it can be left overnight to set in the incubator but make sure there is medium on the outside of the insert so that the epithelial cells do not dry out and die.

Descemet's Membrane

Collagen, Type I, bovine dermal (3.3 mg/ml; 0.8 ml) collagen, Type IV (0.5 mg/ml; 100 µl) and collagen medium, 10× (see below; 0.4 ml) are mixed together gently but well (avoid forming bubbles), and neutralised with 1 N NaOH, if needed. Then, 100 µl of fibronectin is added (1 mg/ml stock) and mixed well.

The resulting solution is added (100–150 µl) to each insert and allowed to set. Again, the inserts should not be moved during the setting process. If reconstructions are being prepared with the endothelium at the bottom, PEG can be mixed into the Descemet's membrane or layered on top as with Bowman's membrane.

Endothelium

Cells are seeded at a concentration of 5 to $7.5 \times 10^4$ per insert in 2 ml of medium per insert. Medium should be replaced as needed.

Air-Liquid Interface

Once the reconstruction is complete, the medium outside the inserts is removed. Since the epithelium is at the bottom of the insert, the cells will be at a air-liquid interface. The cells would be supplemented by medium on the inside of the insert. About 1–2 ml of medium is used with aprotinin and this is replaced regularly (every day or every other day)

| Collagen Buffer (With Serum): | |
| --- | --- |
| 10X HEPES (200 mM HEPES, 100 mM NaOH) | 9 ml; |
| 10X Medium 199 or DMEM | 9 ml; |
| FBS | 10 ml; and |
| Gentamicin. | |
| Collagen Buffer (Serum-free): | |
| 10X HEPES (200 mM HEPES, 100 mM NaOH) | 9 ml; |
| 10X Medium 199 or DMEM | 9 ml; |
| Serum-free medium, 2X | 10 ml; |
| Insulin-transferrin-selenium (Collaborative) | 0.6 ml; |
| Bovine serum albumin | 0.5 g; and |
| Gentamicin. | |

Medium

Once reconstructions are completed, aprotinin is added to the medium for maintaining the cultures (0.07 TIU).

Alternative Methods For Reconstruction

The matrix base of the "stroma" can also be constructed from gelatin (a denatured collagenous material) instead of collagen I, chondroitin sulphate and other matrix components described above.

The fibrin, gelatin matrix of the "sclera" can also be modified for growing the keratocytes of the stroma. This matrix can replace the collagen-based matrix described above.

The matrix supports can be cross-linked for added stability using cross-linking agents such as glutaraldehyde and polyepoxy compounds. Glutaraldehyde can be used for cross-linking and stabilizing the collagen-based matrices. For example, the stromal matrix is prepared as follows for six 30 mm tissue culture inserts. Components are preferably mixed in the following order, mixing gently but very well at each step: Type I collagen (bovine dermal, approx. 3 mg/ml; 6 ml), collagen buffer (1 ml), chondroitin sulphate C (20% in PBS; 520 $\mu$L), retinol acetate (5 mM; 12 $\mu$L).

To the above mixture, 100 $\mu$L of 1% glutaraldehyde in 20% dextran in medium (M199 or DMEM) is added and mixed thoroughly. The mixture is then left to cross-link at room temperature for at least 30 min to 1 hour, taking care that it does not solidify. Unreacted glutaraldehyde is bound up and rendered 'non-toxic' by adding 450 to 500 $\mu$L of 20% glycine in medium, mixing thoroughly and letting the mixture react for at least 30 min. at room temperature. The mixture is neutralised with NaOH if required. After this, stromal cells are mixed in as described previously and the stroma is formed by aliquoting into inserts.

Other forms of fibrillar collagen such as rat tail tendon type I collagen can be successfully substituted, but the mixture should be neutralised before adding chondroitin sulphate or other proteoglycans to prevent unwanted precipitation of collagen-proteoglycan co-polymers.

Polyethylene glycol (PEG) may also be added on its own or within the matrices for Descemet's and Bowman's membranes. The purpose of the PEG is to prevent invasion of stromal cells into the adjacent endothelial and epithelial compartments and overgrowing them.

Addition of a PEG Layer

An aqueous solution of PEG, such as the 2% PEG in medium (e.g. DMEM) is used to create a thin film either between Descemet's membrane and the stroma, and/or between Bowman's membrane and the stroma. The PEG solution is applied to the 'cornea' for 30 min to 1 hour to allow a coating to form. The rest of the solution is carefully aspirated off before adding the next layer.

Adding PEG to Descemet's and/or Bowman's Membrane

PEG can be incorporated into the matrix. For example in Bowman's membrane, the following mixture can be used: type I collagen (bovine dermal; 1.5 mL), collagen buffer (500 $\mu$L), fibronectin (1 mg/ml; 100 $\mu$L) and 20% PEG in collagen buffer (100 $\mu$L), with neutralisation with 1 N NaOH. Other type I collagens such rat tail tendon can also be substituted, but it has been found that bovine dermal collagen gives the best results.

Other non-biological polymers can also be used instead of, or together with, the natural biopolymers. For example, 0.5% to 1% polyvinylpyrollidone (PVP) can be added to the fibrin/thrombin matrix described above in order to strengthen it. Blends and copolymers of naturally occurring extracellular matrix molecules and synthetic monomers (eg. Polyethylene oxide, activated polyethylene glycols, polyurethanes) can also be substituted for the stroma.

DMEM is used without phenol red indicator, instead of Medium 199 (which comes with indicator) when reconstructing corneas for optical measurements. Also, serum-free medium can be substituted for serum-containing medium for the reconstructions.

Although type I collagen and chondroitin sulphate C are preferred, evidence from the literature would suggest that a heterotypic mixture of type I and type V collagen would produce finer fibrils and hence a more transparent matrix. Keratan and dermatan sulphates can also be used to substitute for chondroitin sulphate. Chondroitin sulphates A and B, and also hyaluronate in place of chondroitin sulphate C, have been used in successful reconstructions.

Functional Testing

Stromal Matrix Behavior

Corneal stromal matrix is able to swell by 10 to 20% in thickness, when exposed to hypotonic solutions, e.g. distilled water (Duane's Archives of Ophthalmology). This is due to the high proteoglycan content within the stroma that takes up water. The reconstituted matrix was tested to see if it would behave in a similar manner.

Stromal matrices were reconstituted with glutaraldehyde cross-linking in 12 mm inserts, using 250 $\mu$l per insert.

The inserts were conditioned in the chondroitin sulphate-containing serum-free medium. Both matrix and medium have 1.35% chondroitin sulphate (isomolar). The thickness of the stromal matrix in each insert was measured using Optical Coherence Tomography (OCT), with an instrument from Humphrey Instruments (Div. of Carl Zeiss).

Half of the inserts were removed and placed in distilled water. The controls were retained in the chondroitin sulphate containing medium.

After one hour incubation, the thickness of each sample was re-measured by OCT.

Changes were noted. Student's t-test (2-tailed, assuming statistical significance at P<0.05) was performed to determine whether there were any initial thickness differences between control and experimental samples. T-tests were then performed to determine statistical significance in the samples before after exposure to either medium or distilled water. Six inserts with matrices were used in each group.

Results

There was no significant difference (P=0.277) in thickness between control and experimental matrices.

There was a 0.4% decrease in thickness in control samples that were exposed to medium only. This was not statistically significant (P=0.679).

There was an 8% increase in stromal matrix thickness when placed in distilled water. This increase in thickness was statistically significant (P=0.014).

Endothelial Function

Ouabain, a cardiac glycoside, inhibits Na/K ATPase, disrupting corneal endothelial functioning. When this is applied to the cornea, the endothelium looses its pumping function, and without this, the cornea will swell (Watsky et al. 1990).

1. Corneas were reconstructed in 30 mm inserts. In this experiment, we have contructed them with the epithelium down.
2. A whole cornea was immersed in DMEM only.
3. At the start of the experiment, medium outside insert was removed and replaced with silicone oil. This essentially seals off the epithelium. Corneal thickness was measured using Optical Coherence Tomography (OCT) (Humphrey Instruments, Carl Zeiss, Inc.). Four readings were taken from each cornea and the average was taken.
4. DMEM within the control insert was replaced with 1 ml of fresh DMEM only. Experimental cornea was treated with 10-4M ouabain in DMEM.
5. After 2 hours, the corneal thicknesses were measured by OCT.
6. Changes in corneal thickness (if any) was calculated.

Results

Preliminary results were obtained with one set of corneas. Corneas completely immersed in medium will swell due to stromal edema (Richard et al. 1991). When silicon oil was applied to the epithelium, this formed a barrier to water entry via the epithelium (Watsky et al. 1989). In the corneas exposed to DMEM only, there was a decrease in thickness by 11%. This likely reflects the osmoregulation of the cornea by endothelial cells, i.e. excess water was pumped out. When ouabain was applied, endothelial function was likely disrupted. Hence the cornea swelled by 24%.

Testing of Artificial Corneas

Figure 24A:
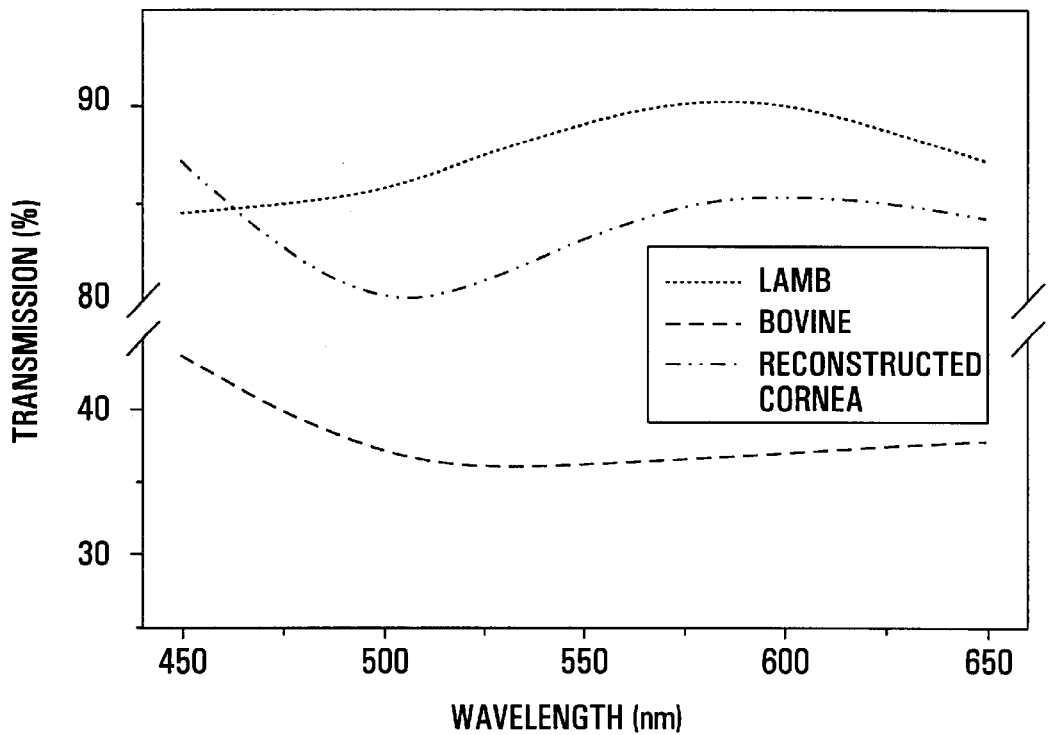
FIG. 24 shows wavelength dependence of transparency and non-specular reflection of excised and reconstructed corneas: Transparency (A) and non-specular reflection (B) of excised animal corneas and reconstructed corneas as a function of wavelength.
Figure 24B:
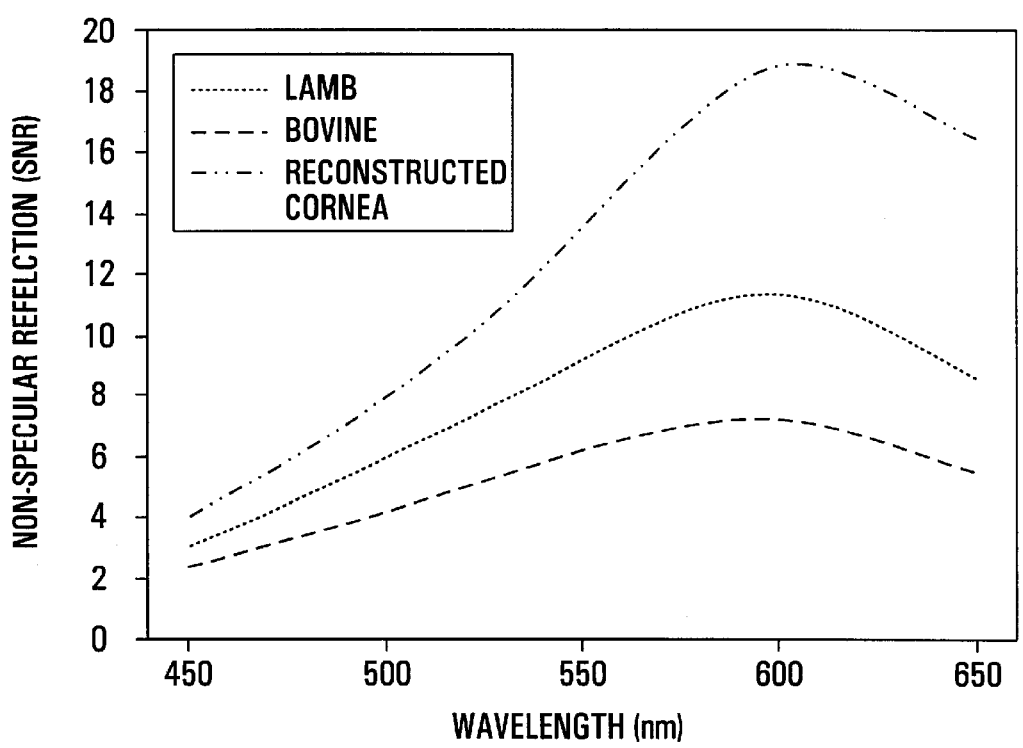

The optical properties of fresh animal (bovine and lamb) and artificial corneas was measured as a function of wavelength to demonstrate cross species differences. Significant differences were observed across species (FIGS. 24) for both transparency and non-specular reflection.

Figure 25A:
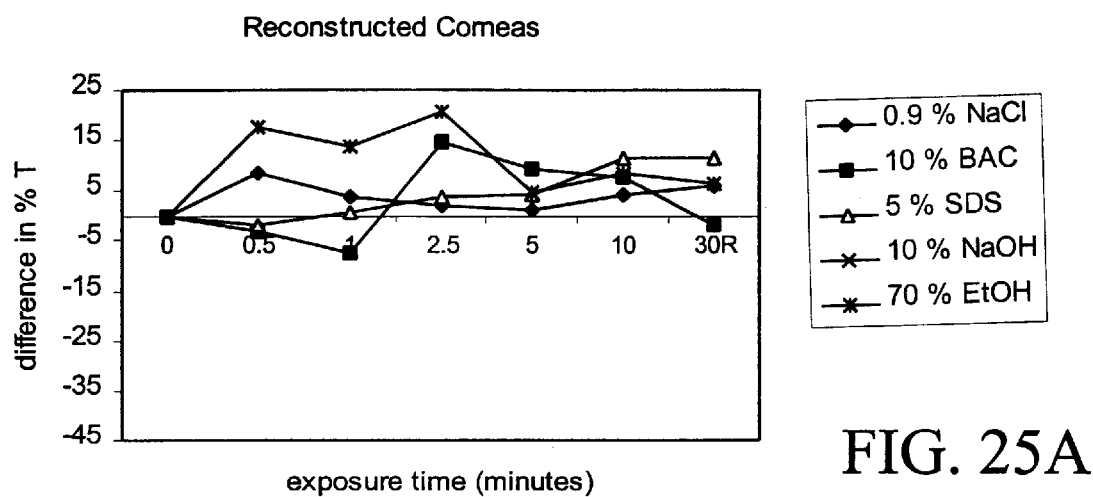
FIG. 25 shows dosage response of animal and reconstructed corneas: Reconstructed (A), rabbit (B) and porcine (C) corneas were exposed to different chemicals and for different exposure times. Transparency was measured with transparent light.
Figure 25B:
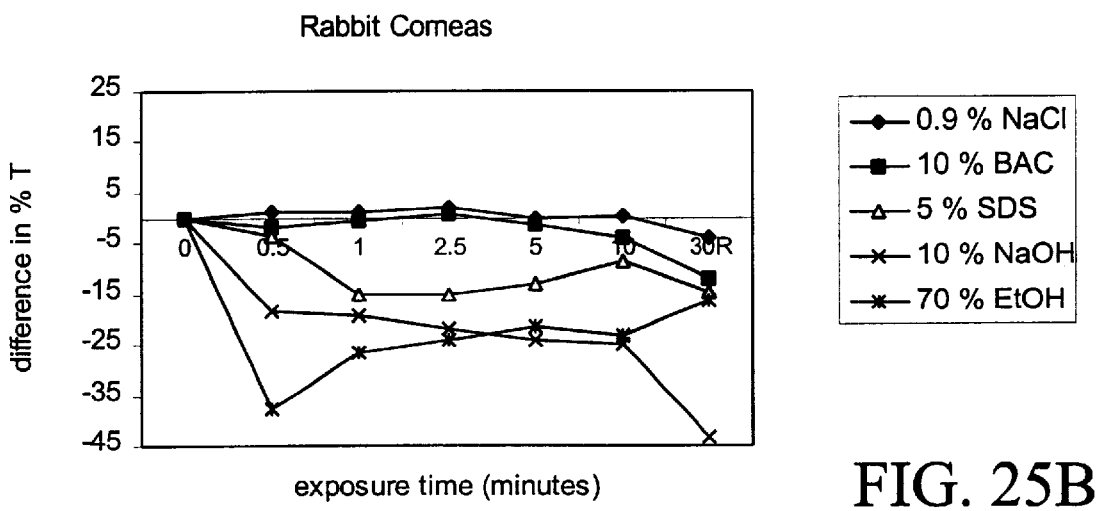
Figure 25C:
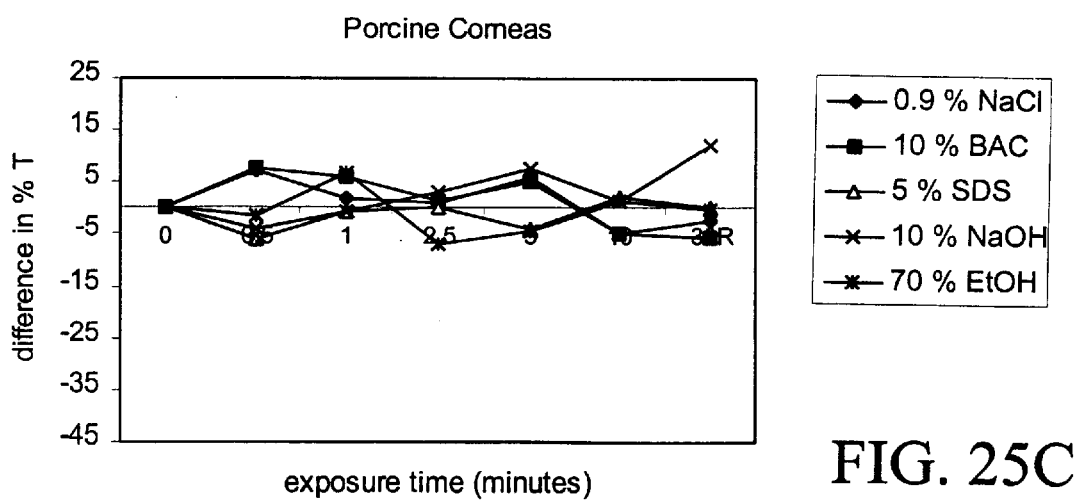
Figure 26B:
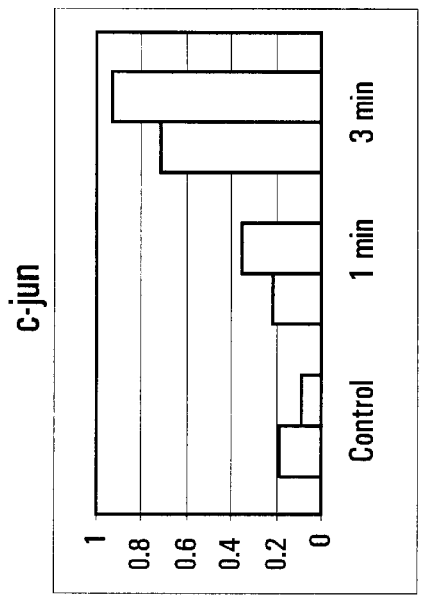
FIG. 26(a–j) shows relative intensities of RT-PCR bands for SDS-treated and untreated human artificial corneas. Band intensities for the indicated genes were quantitated by a phosphoimager and were divided by the intensity of the corresponding GAPDH band. Corneas were treated with 5% SDS in medium for 1 or 3 minutes, then washed twice with medium. Total RNA was extracted at 1 hour after the SDS treatment, and RT-PCR was carried out for specific primers for various genes.
Figure 26D:
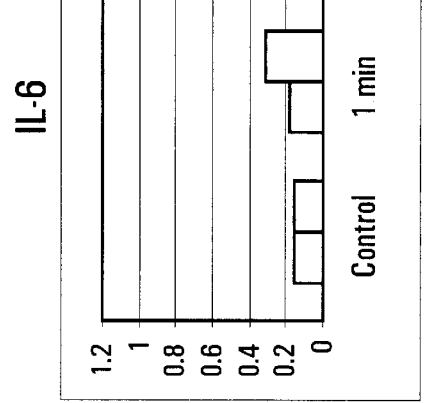
Figure 26A:
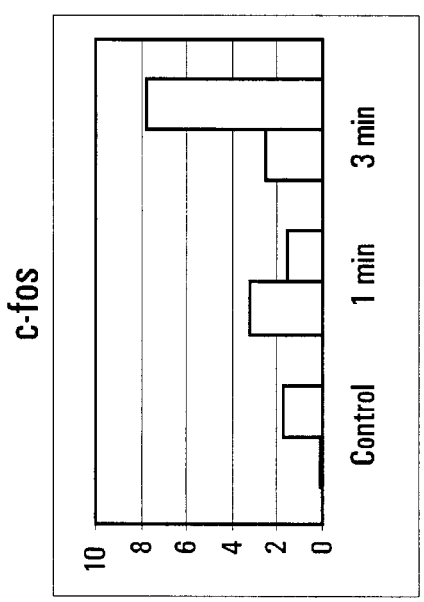
Figure 26C:
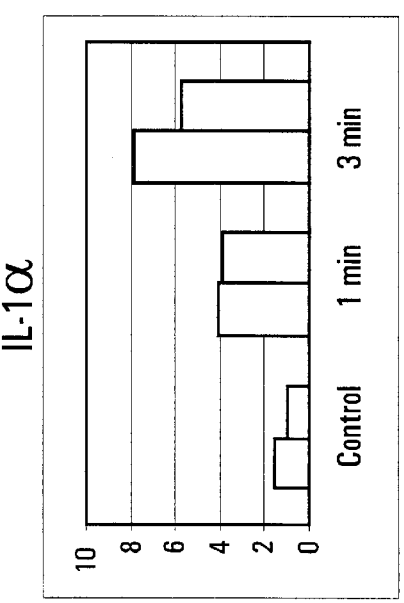
Figure 26F:
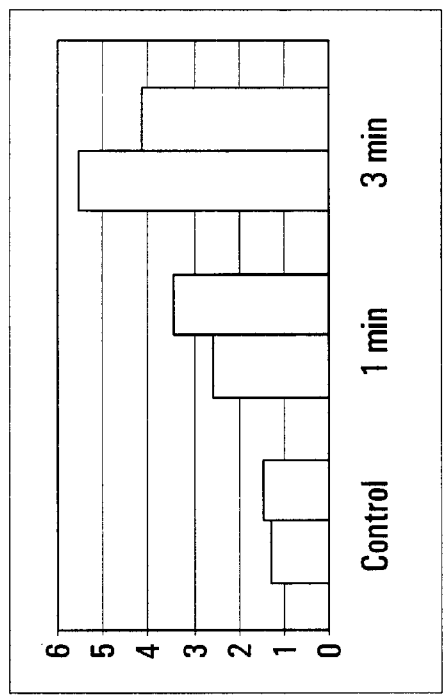
Figure 26H:
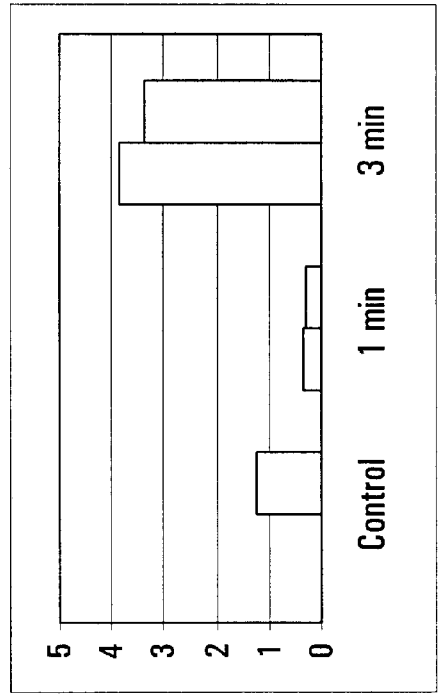
Figure 26E:
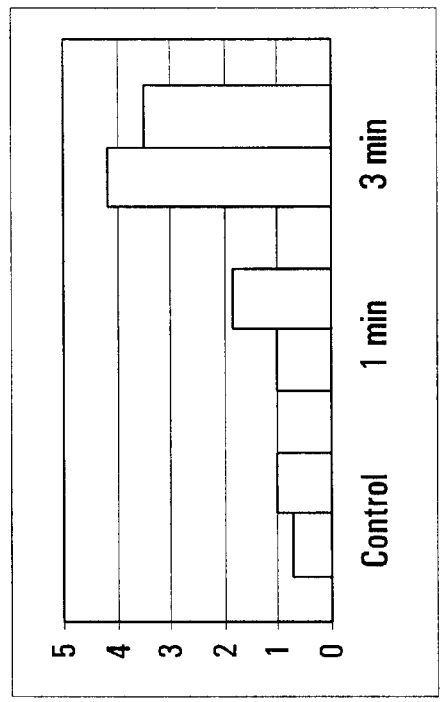
Figure 26G:
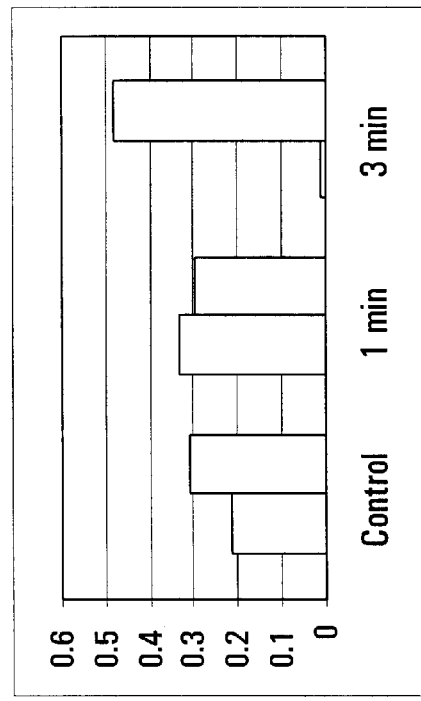
Figure 26J:
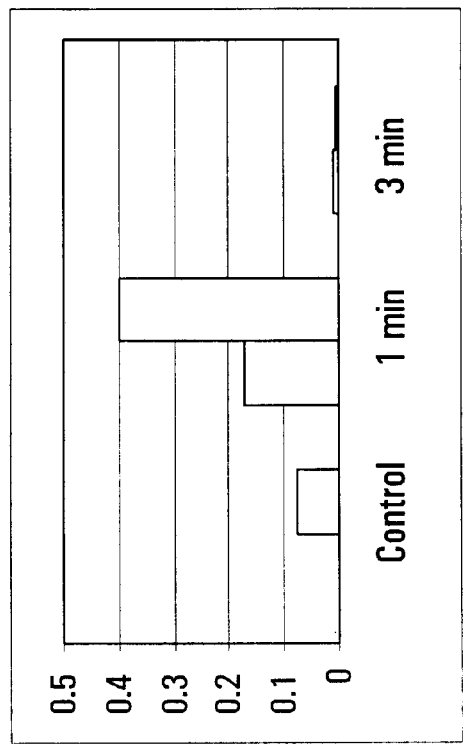
Figure 26I:
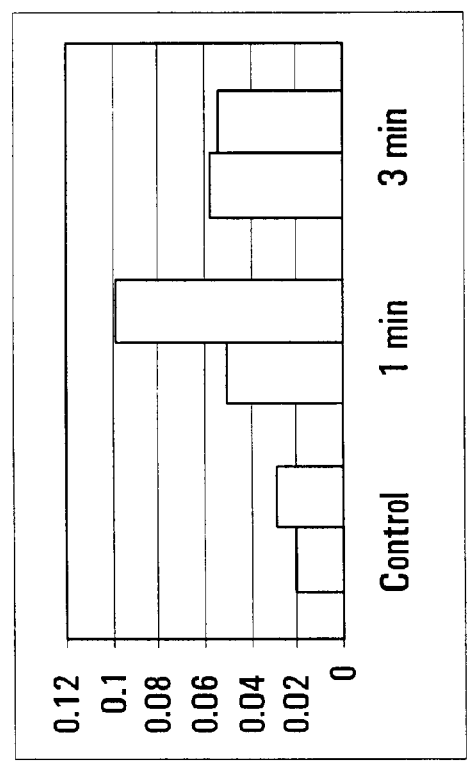

In another experiment, artificial and excised animal (rabbit) corneas were exposed to a variety of chemicals with different degrees of toxicity (FIG. 25). Transparency was measured using white light (from a halogen light source). The duration of the exposure to the toxic agent (30 sec to 10 minutes) was also varied to modulate the response of the cornea for each of the chemicals. In this experiment the optical properties were only measured immediately before and after the exposure to the chemical agent. The results demonstrate that a response can be measured in the artificial cornea. Similarity between porcine and human corneas is reflected in the similarity in response of the porcine and artificial corneas. This also suggests the artificial corneas are functioning like human corneas The results also reflect across-species (rabbit vs artificial cornea data) differences in the response.

The artificial cornea of the invention may be used, in the insert in which it is prepared, for testing for reaction to applied substances. Preferably, corneas are reconstructed so that the epithelium is on the bottom of the insert, against the porous membrane and the endothelium is on top. The air-liquid interface is achieved by removing all medium surrounding and under the insert, while keeping medium within the insert. The insert is preferably fitted with a leak-proof cap. This allows the insert to be filled with a liquid or semi-liquid medium and once the cap is put on, the capped insert can be inverted for testing.

Testing can be done by placing a test substance on top of a porous membrane that is previously placed over the epithelium. The porous membrane mimics the protection normally provided by epithelial tear film.

With this method, other layers of the eye such as iris can be introduced by snapping on other chambers and sealing the whole assembly so that it can be inverted for testing.

Numerous modifications, variations and adaptations may be made to the particular embodiments of the invention described above without departing from the scope of the invention as defined in the claims. All references disclosed herein are hereby incorporated by reference.

References

| U.S. PAT. DOCUMENTS | | |
|---|---|---|
| 5,374,515 | December 1994 | Parenteau et al. |
| 5,585,265 | December 1996 | Kahn et al. |

Other Publications

Anderson, J. A., Richard, N. R., Rock, M. E. and Binder, P. S. 1993. Requirement for vitamin A in long-term culture of human cornea. Invest. Ophthalmol. Vis. Sci. 34: 3442–3449.

Araki-Sasaki, K., Ohashi, Y., Sasabe, T., Hayashi, K., Watanabe, H., Tano, Y. and Handa, H.1995. Invest. Ophthalmol. Vis. Sci. 36: 614–621.

Assil, K. K. and Quantock, A. J. 1993. Wound healing in response to keratorefractive surgery. Surv. Ophthalmol. 38: 289–302.

Bagley, D. M., Bruner, L. H., deSilva, O., Cottin, M., O'Brien, K. A. F., Uttley, M. and Walker, A. P. 1992. An evaluation of five potential alternatives in vitro to the rabbit eye irritation test in vivo. Toxicol. in Vitro 6: 275–284.

Bockman, C., Griffith, C. M., and Watsky, M. A. 1998. Characterization of whole cell ionic currents from cultured human corneal epithelial cells. Invest. Ophthalmol. Vis. Sci. 39: 1143–1151.

Borenfreund, E. and Puerner, J. A. 1985. Toxicity determined in vitro by morphological alterations and neutral red absorption. Toxicol. Lett. 24: 119–124.

Bodnar, A. G., Ouellete, M., Frolkis, M., Holt, S. E., Chiu, C. P., Morin, G. B., Harley, C. B., Shay, J. W., Lichtsteiner, S., and Wright, W. E. 1998. Extension of life-span by introduction of telomerase into normal human cells. Science 279: 349–352.

Burton, A. B. G., York, M. and Lawrence, R. S. 1981. The in vitro assessment of severe eye irritants. Food Cosmet. Toxicol. 19: 471–480.

Collin, H. B., Anderson, J. A., Richard, N. R. and Binder, P. S. 1995. In vitro model for corneal wound healing: organ cultured human corneas. Curr. Eye Res. 14: 331–339.

Doughman, D. J. 1980. Prolonged donor cornea preservation in organ culture: long term clinical evaluation. Trans. Am. Ophthlmol. Soc. LXXCVIII: 624–628.

Draize, J. H., Woodard, G. and Calvery, H. O. 1944. Methods for the study of irritation and toxicity of substances applied topically to the skin and mucuous membranes. J. Pharmacol. Exp. Ther. 82:377–390.

Galer, D. M. 1992. A collaborative approach to the evaluation of alternatives to the eye irritation test using chemical intermediates. In Vitro Cell Dev. Biol 28: T-2.

Gautheron, P., Dukic, M., Alix, D. and Sina, J. F. 1992. Bovine corneal opacity and permeability test: An in vitro assay of ocular irritancy. Fund. Appl. Toxicol. 18: 442–449.

Gordon, V. C. 1992. Utilization of biomacromolecular in vitro assay systems in the prediction of in vivo toxic responses. Lens and Eye Toxicity Res. 9: 211–227.

Griffith, C. M. and Hay, E. D. 1992. Epithelial-mesenchymal transformation during palatal fusion: carboxyfluorescein traces cells at light and electron microscopic levels. Development 116: 1987–1099.

Griffith, M. 1997. Midkine and secondary neurulation. Teratology 55:213–223.

Halbert C. L., Demers, G. W. and Galloway, D. A. 1991. The E7 gene of human papillomavirus type 16 is sufficient for immortalization of human epithelial cells. J. Virol. 65: 473–478.

Halbert, C. L., Demers, G. W. and Galloway, D. A. 1992. The E6 and E7 genes of human pappiloma virus type 6 have weak immortalizing activity in human epithelial cells. J. Virol. 66: 2125–2134.

Heitzmann, J. Binder, P. S., Kassar, B. S., and Nordan, L. T. 1993. The correction of high myopia using the excimer laser. Arch. Ophthalmol. 111: 1627–1634.

Kahn, C. R., Young, E., Lee, I. H. and Rhim, J. S. 1993. Invest. Ophthalmol. Vis. Sci. 34: 1983–1990. Human corneal epithelial primary cultures and cell lines with extended life span: in vitro model for ocular studies.

Martin, K. M. and Stott, C. W. 1992. The trans-epithelial permeability assay as an in vitro assay for predicting ocular irritation of surfactant formulations. In Vitro Cell Dev. Biol. 28: T-1032.

Minami, Y., Sugihara, H. and Oono, S. 1993. Reconstruction of cornea in three-dimensional collagen gel matrix culture. Invest. Ophthal. Vis. Sci. 34: 2316–2324.

Osborne, R., Perkins, M. A. and Roberts, D. A. 1995. Development and intralaboratory evaluation of an in vitro human cell-based test to aid ocular irritancy assessments. Fund. Appl. Toxicol. 28: 139–153.

Rae, J. L., Cooper, K. E., Gates, P. and Watsky, M. A. 1991. Low access perforated patch recordings using amphotericin. Brit. J. Neurosci. Methods 37: 15–26.

Richard, N. R., Anderson, J. A., Weiss, J. L. and Binder, P. S. 1991. Air/liquid corneal organ culture: a light microscopic study. Current Eye Res. 10: 739–749.

Schermer, A., Galvin, S. and Sun, T. T. Differentiation-related expression of a major 64K corneal keratin in vivo and in culture suggests limbal location of corneal epithelial stem cells. J. Cell Biol. 103: 49–62.

Sirois E., Cote, M. F. and Doillon, C. J. 1993. Growth factors and biological support for endothelial cell lining: in vitro study. Int. J. Artificial Organs 16:609–619.

Southern, P. J. and Berg, P. 1982. Transformation of mammalian cells to antibiotic resistance with a bacterial gene under control of the SV40 early region promoter. J. Molec. Appl. Gen. 1: 327–341.

Watsky, M. A., McDermott, M. L. and Edelhauser, H. F. 1989. In vitro corneal endothelial permeability in rabbit and human: The effects of age, cataract surgery and diabetes. Exp. Eye Res. 49: 751–767.

Watsky, M. A., McCartney, M. D., McLaughlin, B. J. and Edelhauser, H. F. 1990. Corneal endothelial junctions and the effect of Ouabain. Inv. Ophthal. Vis. Sci. 31: 933–941.

Watsky, M. A., Cooper, K. E. and Rae, J. L. 1992. A transient outwardly rectifying potassium current in the rabbit corneal endothelium. J. Membrane Biol. 128:123–132.

Zieske, J. D., Mason, V. S., Wasson, M. E., Meunier, S. F., Nolte, C. J. M., Fukai, N, Olsen, B. R. and Parenteau, N. L. 1994. Basement membrane assesmbly and differentiation of cultured corneal cells: Importance of culture environment and endothelial cell interaction. Exp. Cell Res. 214: 621–633.

What is claimed is:

1. An artificial mammalian cornea which comprises:
   a) an endothelium comprising primary or immortalized mammalian endothelium cells;
   b) a crosslinked stromal matrix;
   c) an epithelium comprising primary or immortalized mammalian epithelium cells; and
   d) at least one layer selected from Bowman's membrane and Descemet's membrane.

2. The cornea of claim 1, wherein the stromal matrix comprises primary or immortalized mammalian stroma cells.

3. The cornea of claim 1, wherein at least one of a) through c) comprises immortalized cells.

4. The cornea of claim 2, wherein at least one of a) through c) comprises immortalized cells.

5. The cornea of claim 1, wherein at least one of a) through c) comprises immortalized human cells.

6. The cornea of claim 2, wherein at least one of a) through c) comprises immortalized human cells.

7. The cornea of claim 1, wherein all of a) through c) comprise immortalized cells.

8. The cornea of claim 2, wherein all of a) through c) comprise immortalized cells.

9. The cornea of claim 1, wherein all of a) through c) comprise immortalized human cells.

10. The cornea of claim 2, wherein all of a) through c) comprise immortalized human cells.

11. The cornea of claim 1, wherein Bowman's membrane and Descemet's membrane are present.

12. The cornea of claim 2, wherein Bowman's membrane and Descemet's membrane are present.

13. The cornea of claim 1, wherein Bowman's membrane comprises Type I collagen.

14. The cornea of claim 2, wherein Bowman's membrane comprises Type I collagen.

15. The cornea of claim 1, which further comprises an artificial sclera comprising primary or immortalized mammalian angiogenic cells.

16. The cornea of claim 2, which further comprises an artificial sclera comprising primary or immortalized mammalian angiogenic cells.

17. The cornea of claim 15, wherein the angiogenic cells are human umbilical vein endothelial cells (HUVECs).

18. The cornea of claim 16, wherein the angiogenic cells are human umbilical vein endothelial cells (HUVECs).

19. The cornea of claim 1, wherein the cornea is an artificial human cornea.

20. The cornea of claim 1, wherein the epithelium cells are corneal cells.

21. The cornea of claim 1, wherein the endothelium cells are corneal cells.

22. The cornea of claim 1, wherein gluteraldehyde is used to crosslink the stromal matrix.

23. A method for preparing an artificial mammalian cornea, which comprises the following steps:
   a) growing an endothelium which comprises primary or immortalized mammalian endothelium cells;
   b) optionally layering a Descemet's membrane on the endothelium;
   c) forming a stromal matrix on the endothelium or on the Descemet's membrane, if present;
   d) optionally layering a Bowman's membrane on the stromal matrix; and
   e) growing an epithelium, which comprises primary or immortalized mammalian epithelium cells, on the stromal matrix or on the Bowman's membrane, if present, wherein at least one of steps b) or d) must be present; or, a) growing an epithelium which comprises primary or immortalized mammalian epithelium cells;

b) optionally layering a Bowman's membrane on the epithelium;

c) forming a stromal matrix on the epithelium or on the Bowman's membrane, if present;

d) optionally layering a Descemet's membrane on the stromal matrix; and e) growing an endothelium, which comprises primary or immortalized mammalian endothelium cells, on the stromal matrix or on the Descemet's membranes if present;

wherein at least one of steps b) or d) must be present.

24. The method of claim 23, which includes the step of crosslinking the stromal matrix.

25. The method of claim 24, wherein gluteraldehyde is used to crosslink the stromal matrix.

26. The method of claim 25, which includes the step of washing the crosslinked stromal matrix with glycine.

27. The method of claim 23, which includes:

i) growing an artificial sclera, which comprises primary or immortalized mammalian angiogenic cells, around a resilient removable plug;

ii) removing the plug and inserting the endothelium, the optional Descemet's membrane and the stromal matrix, wherein the stromal matrix is essentially co-planar with the artificial sclera to receive the optional Bowman's membrane;

iii) optionally layering the Bowman's membrane on the stromal matrix and the artificial sclera;

iv) growing the epithelium on the stromal matrix and sclera or the Bowman's membrane, if present.

28. The method of claim 23, which includes, in step c, additionally forming an artificial sclera co-planar with the stromal matrix which artificial sclera comprises primary or immortalized mammalian angiogenic cells.

29. An artificial mammalian cornea which comprises:

a) a crosslinked stromal matrix;

b) Bowman's membrane; and c) Descemet's membrane.

30. The cornea of claim 29, which further comprises an artificial sclera comprising primary or immortalized mammalian angiogenic cells.

31. The cornea of claim 30, wherein the angiogenic cells are human umbilical vein endothelial cells (HUVECs).

32. The cornea of claim 29, wherein the cornea is an artificial human cornea.

33. The cornea of claim 29, wherein gluteraldehyde is used to crosslink the stromal matrix.

* * * * *

UNITED STATES PATENT AND TRADEMARK OFFICE
CERTIFICATE OF CORRECTION

PATENT NO.    : 6,645,715 B1
DATED         : November 11, 2003
INVENTOR(S)   : May Griffith et al.

It is certified that error appears in the above-identified patent and that said Letters Patent is hereby corrected as shown below:

<u>Column 27,</u>
Line 12, replace "membranes" with -- membrane, --.

Signed and Sealed this

Twenty-fourth Day of February, 2004

JON W. DUDAS
*Acting Director of the United States Patent and Trademark Office*